US012605123B2

(12) United States Patent
Nishizaka

(10) Patent No.: US 12,605,123 B2
(45) Date of Patent: Apr. 21, 2026

(54) INFORMATION PROCESSING METHOD, NON-TRANSITORY COMPUTER READABLE STORAGE MEDIUM, AND INFORMATION PROCESSING DEVICE FOR CONTROLLING OUTPUT OF WARNINGS RELATED TO DETECTED EXERCISE CONDITION

(71) Applicant: CASIO COMPUTER CO., LTD., Tokyo (JP)

(72) Inventor: Nobuyoshi Nishizaka, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 511 days.

(21) Appl. No.: 18/103,576

(22) Filed: Jan. 31, 2023

(65) Prior Publication Data
US 2023/0255570 A1 Aug. 17, 2023

(30) Foreign Application Priority Data
Feb. 17, 2022 (JP) ................................. 2022-022517

(51) Int. Cl.
*A61B 5/00* (2006.01)
*A61B 5/024* (2006.01)
*A61B 5/11* (2006.01)

(52) U.S. Cl.
CPC .............. *A61B 5/746* (2013.01); *A61B 5/024* (2013.01); *A61B 5/11* (2013.01); *A61B 2503/10* (2013.01); *A61B 2505/09* (2013.01)

(58) Field of Classification Search
CPC ........... A61B 5/746; A61B 5/024; A61B 5/11; A61B 2503/10; A61B 2505/09;
(Continued)

(56) References Cited

U.S. PATENT DOCUMENTS 6,405,077 B1 * 6/2002 Birnbaum .......... A61B 5/02455
128/905
9,299,235 B2 3/2016 Kasama
(Continued)

FOREIGN PATENT DOCUMENTS

JP 2013232806 A 11/2013
JP 2014045783 A 3/2014
(Continued)

OTHER PUBLICATIONS

Extended European Search Report (EESR) dated Jun. 22, 2023, issued in counterpart European Application No. 23150749.2.

*Primary Examiner* — Omar Casillashernandez
(74) *Attorney, Agent, or Firm* — Holtz, Holtz & Volek PC

(57) ABSTRACT
Provided is an information processing method, a program, and an information processing device capable of limiting a warning function more appropriately. The information processing method performed by a computer includes: determining whether an execution condition is satisfied, the execution condition including at least one of a first condition related to the length of time during which a warning is generated by a predetermined normal warning function as a warning function related to an exercise state of a subject when performing a certain exercise; a second condition related to the fatigue level of the subject; a third condition that the content of the certain exercise being performed by the subject is not a certain content; a fourth condition related to the possibility of achieving the goal related to the certain exercise of the subject; and a fifth condition related to an athletic ability of the subject; and performing a limiting process of controlling the warning function so that the warning is more limited than in the case of the normal warning function, on the condition that the execution condition is satisfied.

21 Claims, 7 Drawing Sheets

(58) Field of Classification Search

CPC ... A61B 5/1112; A61B 5/1118; A61B 5/1123; A61B 5/486; A61B 5/02438; A61B 5/0205; A61B 5/1117; A61B 5/681; A61B 5/6898; A61B 5/7275; A61B 2562/0219; A61B 2562/0223; G16H 40/63; G08B 21/043; G08B 21/0446

USPC ...................................................... 340/573.1

See application file for complete search history.

(56) References Cited

U.S. PATENT DOCUMENTS

| | | | |
|---|---|---|---|
| 10,867,013 B2 | 12/2020 | Sazuka et al. | |
| 2003/0139778 A1* | 7/2003 | Fischell | A61B 5/358 |
| | | | 607/9 |
| 2007/0288157 A1* | 12/2007 | Peterman | G01C 21/30 |
| | | | 455/404.1 |
| 2012/0029300 A1* | 2/2012 | Paquet | A61B 5/6833 |
| | | | 600/300 |
| 2012/0316406 A1* | 12/2012 | Rahman | G01C 22/006 |
| | | | 600/595 |
| 2015/0094831 A1* | 4/2015 | Brumback | G16Z 99/00 |
| | | | 700/91 |
| 2017/0311903 A1* | 11/2017 | Davis | A61B 5/14532 |

FOREIGN PATENT DOCUMENTS

| | | | |
|---|---|---|---|
| JP | 2016214499 A | 12/2016 | |
| JP | 2019216798 A | 12/2019 | |

\* cited by examiner

FIG. 5

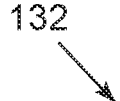
132

<DATA RELATED TO WARNING TARGET INDEX>

| WARNING TARGET INDEX | STRIDE |
|---|---|
| INITIAL UPPER LIMIT OF NORMAL RANGE (cm) | 130 |
| INITIAL LOWER LIMIT OF NORMAL RANGE (cm) | 120 |
| ADJUSTED UPPER LIMIT OF NORMAL RANGE (cm) | 120 |
| ADJUSTED LOWER LIMIT OF NORMAL RANGE (cm) | 110 |

<DATA RELATED TO EXECUTION CONDITION OF LIMITING PROCESS>

| | | |
|---|---|---|
| DETERMINATION TIME (min) | VALUE FOR NORMAL PERIOD | 20 |
| | VALUE FOR CONDITION RELAXATION PERIOD | 10 |
| | LOW FATIGUE OR HIGH PACE PERIOD | 30 |
| | CASE OF HIGH POSSIBILITY OF ACHIEVING GOAL OR HIGH ATHLETIC ABILITY | 60 |
| FIRST THRESHOLD VALUE FOR PULSE RATE DETERMINATION (bpm) | | 176 |
| SECOND THRESHOLD VALUE FOR PACE DETERMINATION (min/km) | | 5 |
| THIRD THRESHOLD VALUE FOR POSSIBILITY OF ACHIEVING GOAL (%) | | 50 |
| FULL MARATHON COMPLETION TIME | | THREE HOURS AND 45 MIN |
| REFERENCE NUMBER OF TIMES FOR NORMAL RANGE ADJUSTMENT | | 2 |

INFORMATION PROCESSING METHOD, NON-TRANSITORY COMPUTER READABLE STORAGE MEDIUM, AND INFORMATION PROCESSING DEVICE FOR CONTROLLING OUTPUT OF WARNINGS RELATED TO DETECTED EXERCISE CONDITION

BACKGROUND OF THE INVENTION

Field of the Invention

The present disclosure relates to an information processing method, a non-transitory computer readable storage medium, and an information processing device.

Description of the Related Art

Conventionally, there is a technique of detecting the exercise state of a subject by using a device carried by a subject such as a test subject or a device attached to the subject and then warning the subject in the case where the detected exercise state is not within a predetermined range. For example, Japanese Unexamined Patent Application Publication No. 2013-232806 discloses a technique of determining that a subject may fall and then warning the subject in the case where the detected acceleration in the direction of gravitational acceleration is equal to or less than a threshold value. It also discloses a technique of limiting the warning function so that it does not warn the subject more than necessary when the subject is walking in a condition where the acceleration tends to be smaller, by making the threshold value smaller as the subject's walking pitch is smaller.

SUMMARY OF THE INVENTION

An information processing device, including:

one or more processors; and one or more memories storing a program to be executed by the one or more processors;

wherein the program causes the one or more processors to perform the following:

determining whether an execution condition is satisfied, the execution condition including at least one of a first condition related to the length of time during which a warning is generated by a predetermined normal warning function as a warning function related to an exercise state of a subject when performing a certain exercise; a second condition related to the fatigue level of the subject; a third condition that the content of the certain exercise being performed by the subject is not a certain content; a fourth condition related to the possibility of achieving the goal related to the certain exercise of the subject; and a fifth condition related to an athletic ability of the subject; and performing a limiting process of controlling the warning function so that the warning is more limited than in the case of the normal warning function, on the condition that the execution condition is satisfied.

Further features of the present disclosure will become apparent from the following description of exemplary embodiments with reference to the attached drawings.

BRIEF DESCRIPTION OF THE DRAWINGS

FIG. 5 is a diagram illustrating an example of the contents of warning setting data.

DESCRIPTION OF THE EMBODIMENTS

Hereinafter, the embodiments of the present disclosure are described on the basis of drawings.

<Configuration of an Exercise Support System>

Figure 1:
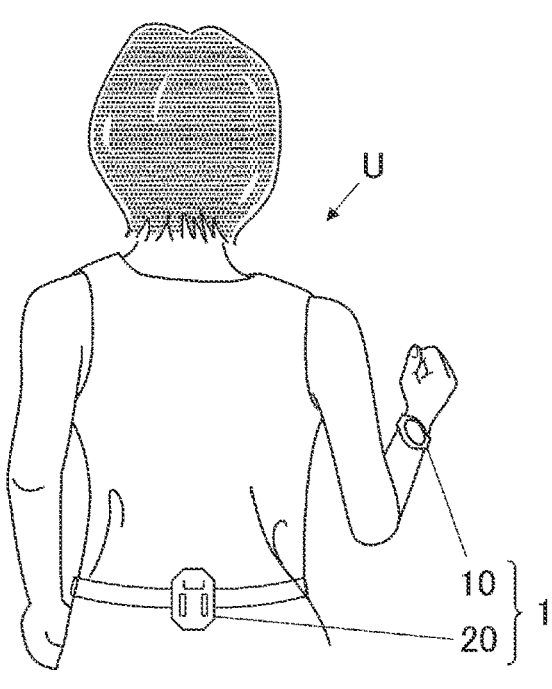
FIG. 1 is a diagram illustrating an exercise support system.

FIG. 1 is a diagram illustrating an exercise support system 1 of this embodiment.

The exercise support system 1 (information processing system) includes a terminal device 10 (information processing device) and a sensor device 20. The exercise support system 1 acquires information on the exercise state of a user U (subject) by using the sensor device 20 attached to the body of the user U. Moreover, the exercise support system 1 presents the acquired information on the exercise state and the information obtained by analyzing the exercise state (such as an advice on the exercise for the user U) to the user U via the terminal device 10 to support the exercise of the user U. The exercise that the user U performs is, for example, walking or running. In this embodiment, the invention is described by using an example that the exercise support system 1 supports the user in running (traveling) as a user's exercise. Exercise states related to running as an exercise include, for example, a moving distance, a moving speed (pace), various kinematic indices related to the body movements of the user U, and the like.

The sensor device 20 is a wearable terminal that is attached to the body of the user U (for example, waist). The sensor device 20 has a sensor unit 24 (see FIG. 3) that detects the exercise state of its own device, and the sensor unit 24 detects the body movements according to the exercise of the user U to whom the sensor device 20 is attached and derives the values of the kinematic indices related to the body movements.

For example, "pitch," "stride," "vertical motion," and "lateral motion" are considered as the kinematic indices in the case of running as the exercise of the user U.

The "pitch" is the number of steps per minute.

The "stride" is a distance from a ground contact (the foot [sole] of the user U coming in contact with the ground) to the next ground contact in one step.

The "vertical motion" is the magnitude of a difference between the highest and lowest points of the center of gravity of the body of the user U or the waist position of the user U during one cycle of running (the time period from one ground contact of a foot to the next ground contact thereof).

The "lateral motion" is the magnitude of the swing of the body's center of gravity or the position of the waist in the horizontal direction during one cycle.

These are examples of kinematic indices, and any indices of the body movements detectable by the sensor device 20 may be used as the kinematic indices.

The sensor device 20, which includes a location information acquisition unit 25 (see FIG. 3) that acquires the location information of its own device, derives the moving distance, the moving speed, and the like of the user U, to whom the sensor device 20 is attached, on the basis of the location information acquired by the location information acquisition section 25.

In addition, the sensor device 20 is capable of sending and receiving data to and from the terminal device via wireless communication (for example, short-range wireless communication such as Bluetooth [registered trademark]). The sensor device 20 generates exercise data including information related to the exercise state of the user U (information on the kinematic indices, the moving distance, the moving speed, and the like) and sends the exercise data to the terminal device 10.

The terminal device 10 is a device that the user U carries while running. In this embodiment, the description is made by giving an example of a smart watch (electronic watch) worn on the wrist of the user U to be used as the terminal device 10. The terminal device 10 may be any other wrist-type terminal worn on the wrist in use, or any other device worn on a part of the body other than the wrist (for example, the arm) in use. It may also be a device that is carried by the user U without being attached to the body of the user U. For example, the terminal device 10 may be a smartphone. The terminal device 10 may also be capable of sending and receiving information to and from an external server, and information on the exercise state of the user U may be sent from the terminal device 10 to the server and recorded on the server. The server may analyze the information on the exercise state, and the terminal device 10 may receive the analysis results and present them to the user.

In the terminal device 10, an application program for providing the user with a service to support the user's exercise (hereinafter, referred to as "exercise application 131" [program] [see FIG. 2]) is installed. In the state where the exercise application 131 is running (in other words, on the exercise application 131), the terminal device 10 displays various information on the exercise state on the basis of the exercise data received from the sensor device 20, and also displays the analysis results of the exercise state. Specifically, the terminal device 10 displays information such as the moving distance of running, the remaining distance, the moving speed (pace), and the kinematic indices described above, as information on the exercise state. The information displayed by the terminal device 10, however, is not limited thereto.

In addition, the terminal device 10 has a warning function that generates a warning (an alert or a notification) related to the exercise state to the user U on the exercise application 131 during running. In detail, the terminal device 10 has a warning unit 14 (see FIG. 2) to implement the warning function, and in the case where a certain index related to a preset exercise state (hereinafter, referred to as "warning target index") is out of the predetermined normal range, the warning unit 14 warns the user. The warning target index may be one of the kinematic indices described above or may be the moving speed (pace) or the like. The user U is able to recognize that his/her running index is out of the normal range by the warning, and is able to improve his/her subsequent running by referring to the warning.

<Configuration of Terminal Device>

Figure 2:
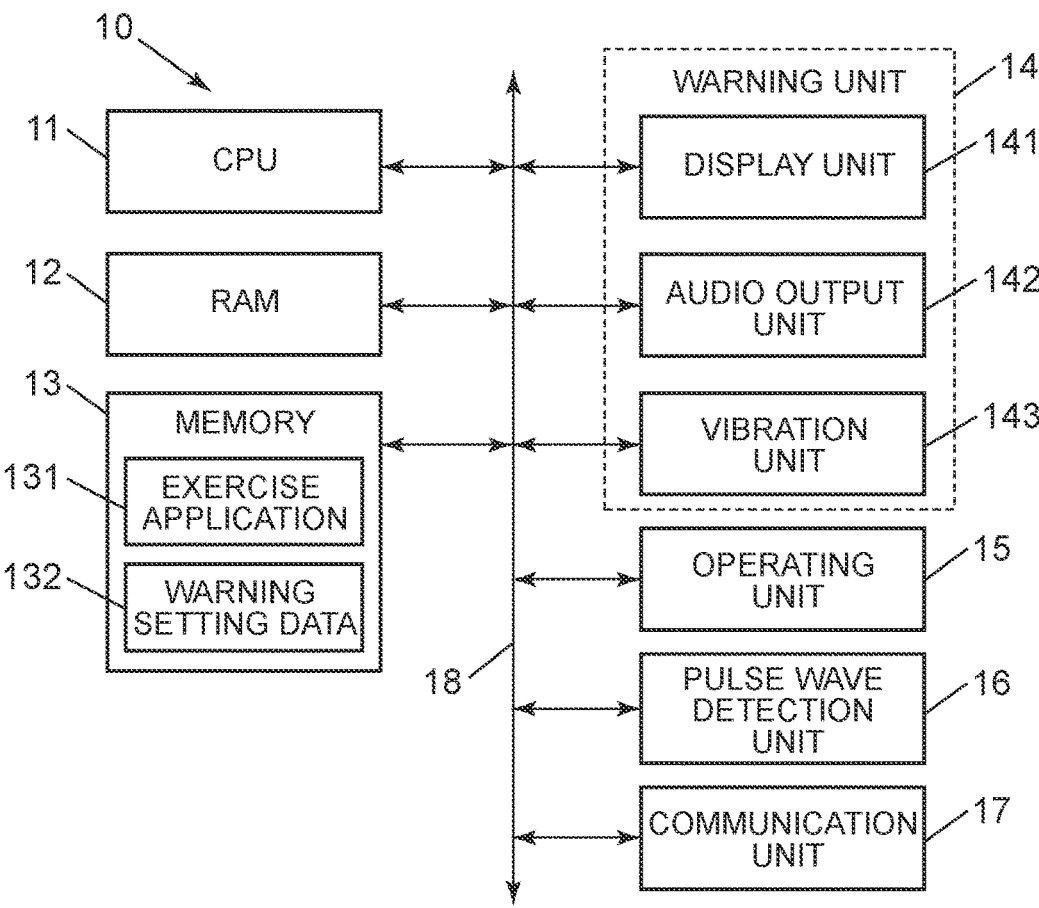
FIG. 2 is a block diagram illustrating a functional configuration of a terminal device.

FIG. 2 is a block diagram illustrating the functional configuration of the terminal device 10.

The terminal device 10 includes a central processing unit (CPU) 11, a random access memory (RAM) 12, a memory 13, a display unit 141, an audio output unit 142, a vibration unit 143, an operating unit 15, a pulse wave detection unit 16, a communication unit 17, and a bus 18. The respective units of the terminal device 10 are connected to each other via the bus 18.

The CPU 11 is a processor that reads and executes the exercise application 131 stored in the memory 13, and controls the operations of the respective units of the terminal device 10 by performing various arithmetic operations. In this embodiment, the CPU 11 corresponds to a "computer" (processing unit). Note that the "computer" may have a plurality of processors (for example, a plurality of CPUs), and a plurality of processes performed by the CPU 11 in this embodiment may be performed by the plurality of processors. In this case, the plurality of processors corresponds to the "computer." In this case, the plurality of processors may be involved in a common process, or the plurality of processors may independently perform different processes in parallel.

The RAM 12 provides the CPU 11 with a working memory space and stores temporary data.

The memory 13 is a non-transitory computer readable storage medium by the CPU 11 as a computer, and stores the exercise application 131 and other programs and various data. The memory 13 includes a non-volatile memory such as a flash memory, for example. The exercise application 131 is stored in the memory 13 in the form of a computer-readable program code. The data stored in the memory 13 includes warning setting data 132, which is referred to in the above-mentioned process for warning. The specific contents of the warning setting data 132 are described later.

The display unit 141 displays the operation screen of the exercise application 131, various information on the exercise state described above, and information on warning, under the control of the CPU 11. For example, a liquid crystal display device that performs display in a dot matrix format is able to be used as the display unit 141, but the display unit 141 is not limited thereto.

The audio output unit 142 outputs a predetermined sound, such as a beep sound, according to the control by the CPU 11.

The vibration unit 143 has a vibrator that vibrates according to the control by the CPU 11. The vibration of the vibrator of the vibration unit 143 is propagated to the housing of the terminal device 10. The user U wearing the terminal device 10 is able to recognize the vibration propagated to the housing with his/her wrist.

The display unit 141, the audio output unit 142, and the vibration unit 143 constitute the warning unit 14 that generates the warning described above. The warning unit 14 warns the user U by a combination of a display on the display unit 141, an audio output by the audio output unit 142, and a vibration by the vibration unit 143.

The configuration of the warning unit 14 is not limited to the configuration illustrated in FIG. 2, and at least one of the audio output unit 142 and the vibration unit 143 may be omitted. In the case where the warning unit 14 has at least one of the audio output unit 142 and the vibration unit 143, the warning unit 14 may not include the display unit 141. In other words, at least one of sound and vibration may be used for warning. In addition to the display unit 141, the audio output unit 142, and the vibration unit 143, the warning unit 14 may also have a configuration for warning such as, for example, a light emitting unit that performs warning by emitting light.

The operating unit 15 accepts a user's input operation and outputs an input signal corresponding to the input operation to the CPU 11. The operating unit 15 has a touch panel superimposed on the display screen of the display unit 141, and detects the touch of a user's finger or the like as an input operation by this touch panel. The operating unit 15 may include a hardware button together with or instead of the touch panel, and may be able to accept an input operation with the hardware button.

The pulse wave detection unit 16 detects the pulse wave of the user U wearing the terminal device 10. The pulse wave detection unit 16 includes a light emitter that emits infrared light from the back cover of the housing of the terminal device 10 (a member that contacts the wrist of the user U when the user U wears the terminal device 10) toward the outside, and a light receiver for use in receiving the reflected light from the skin of the user U. A part of the infrared light emitted from the light emitter and applied to the user's skin is absorbed by the blood in the blood vessels. Therefore, the amount of reflected light from the skin received by the light receiver changes over time in accordance with changes in the blood flow rate due to the pulsation of the heart. The pulse wave detection unit 16 detects pulse waves on the basis of these changes in the amount of light received and outputs data related to the detection results to the CPU 11. The CPU 11 derives the heart rate (pulse rate) of the user U on the basis of the data received from the pulse wave detection unit 16. The heart rate corresponds to the "subject's biometric information."

The communication unit 17 performs a communication operation according to a predefined communication standard. With this communication operation, the communication unit 17 sends and receives data to and from the sensor device 20 by wireless communication (in this embodiment, Bluetooth as a short-range wireless communication).

<Configuration of Sensor Device>

Figure 3:
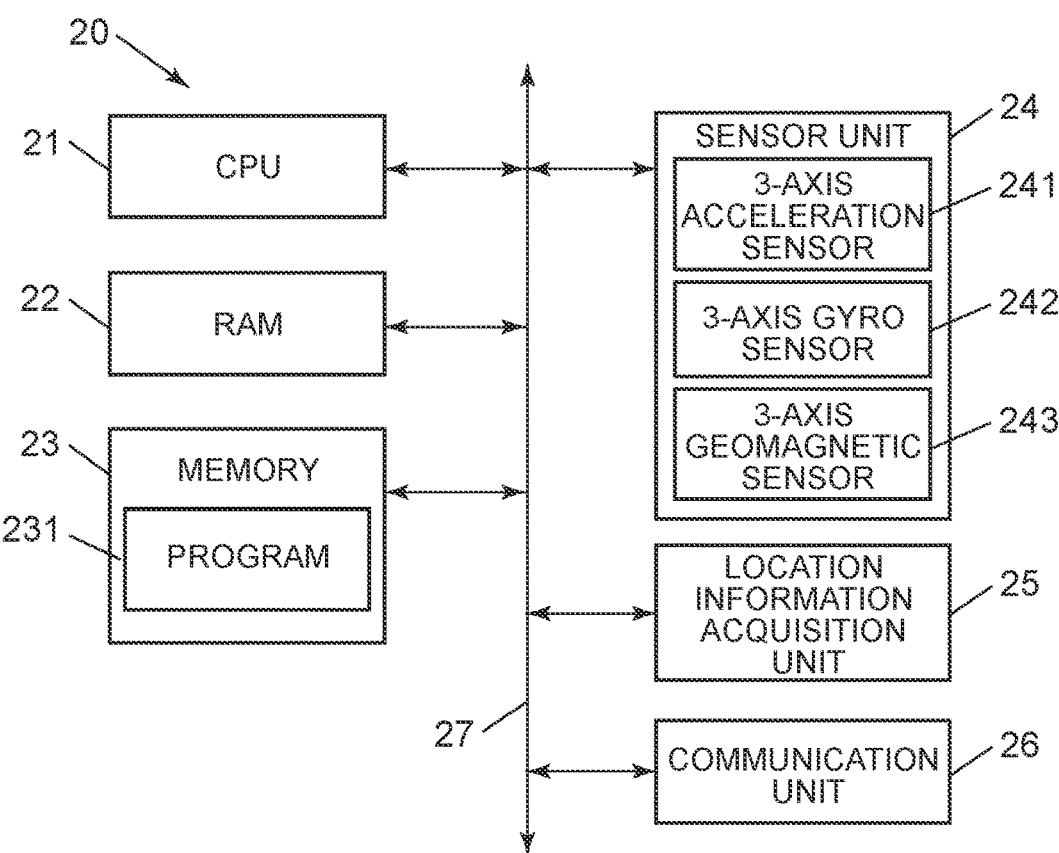
FIG. 3 is a block diagram illustrating a functional configuration of a sensor device.

FIG. 3 is a block diagram illustrating a functional configuration of the sensor device 20.

The sensor device 20 includes a CPU 21, a RAM 22, a memory 23, a sensor unit 24, a location information acquisition unit 25, a communication unit 26, a bus 27, and the like. The respective units of the sensor device 20 are connected to each other via the bus 27.

The CPU 21 is a processor that reads and executes a program 231 stored in the memory 23, and controls the operations of the respective units of the sensor device 20 by performing various arithmetic operations. Note that the sensor device 20 may have a plurality of processors (for example, a plurality of CPUs), and a plurality of processes performed by the CPU 21 of this embodiment may be performed by the plurality of processors. In this case, the plurality of processors may be involved in a common process, or the plurality of processors may independently perform different processes in parallel.

The RAM 22 provides a working memory space to the CPU 21 and stores temporary data.

The memory 23 is a non-transitory recording medium readable by the CPU 21 as a computer, and stores a program 231 and various data. The memory 23 includes a non-volatile memory, such as a flash memory, for example. The program 231 is stored in the memory 23 in the form of a computer-readable program code.

The sensor unit 24 includes a 3-axis acceleration sensor 241, a 3-axis gyro sensor 242, and a 3-axis geomagnetic sensor 243. The 3-axis acceleration sensor 241 detects acceleration in each axis direction applied to the sensor device 20 according to the user's exercise with a predetermined sampling frequency, and outputs acceleration data to the CPU 21 as a detection result. The 3-axis gyro sensor 242 detects an angular velocity around each axis applied to the sensor device 20 according to the user's exercise at a predetermined sampling frequency, and outputs angular velocity data to the CPU 21 as a detection result. The 3-axis geomagnetic sensor 243 detects the direction of the geomagnetic field passing through the sensor device 20 at a predetermined sampling frequency and outputs the geomagnetic data to the CPU 21 as a detection result. The data output from the 3-axis acceleration sensor 241, the 3-axis gyro sensor 242, and the 3-axis geomagnetic sensor 243 include respective signal components for the three mutually orthogonal axes. The sensor unit 24 includes an amplifier, which is not illustrated, that amplifies the analog signals output from the 3-axis acceleration sensor 241, the 3-axis gyro sensor 242, and the 3-axis geomagnetic sensor 243, respectively, and an AD converter, which is not illustrated, that converts the amplified analog signal into digital data and outputs the digital data to the CPU 21. Based on the detection result obtained by the sensor unit 24, the CPU 21 derives the values of the kinematic indices related to the body movements of the user U.

The sensor unit 24 is not limited to the configuration with the 3-axis acceleration sensor 241, the 3-axis gyro sensor 242, and the 3-axis geomagnetic sensor 243, as long as the sensor unit 24 is capable of detecting the body movements of a user wearing the sensor device 20. For example, in the case where the sensor unit 24 includes the 3-axis geomagnetic sensor 243, the 3-axis geomagnetic sensor 243 may be used as a magnetic gyro, instead of the 3-axis gyro sensor 242, to detect the magnitude of the angular velocity around each axis.

The location information acquisition unit 25 calculates the current position by receiving and decoding radio waves transmitted from positioning satellites of the global navigation satellite system (GLASS) such as the global positioning system (GPS). The location information acquisition unit 25 calculates the current position under the control of the CPU 21 and outputs the result to the CPU 21.

The method of calculating the current position by the location information acquisition unit 25 is not limited to the method using the transmitted radio waves from the positioning satellite. For example, the current position may be calculated by a method of identifying the positional relationship with a beacon placed at a predetermined position on the basis of the signals from the beacon, for example.

The communication unit 26 performs a communication operation according to a predefined communication standard. The communication unit 26 performs the communication operation to send and receive data to and from the terminal device 10 via wireless communication (in this embodiment, Bluetooth as short-range wireless communication).

In addition to the configuration described above, the sensor device 20 may include, for example, an operating unit for accepting instructions (reports) of the start and completion of the user's exercise.

<Operation of Exercise Support System>

Subsequently, the operation of the exercise support system 1 is described, focusing on the operation related to warning performed by the terminal device 10.

As described above, the terminal device 10 warns the user U with the warning unit 14 in the case where a predetermined warning target index deviates from the predefined normal range while the user U is running. In this embodiment, the size of the running stride is assumed to be preset as the warning target index. The default lower limit of the normal range of the stride is assumed to be 120 cm, and the default upper limit is assumed to be 130 cm.

Figure 4:
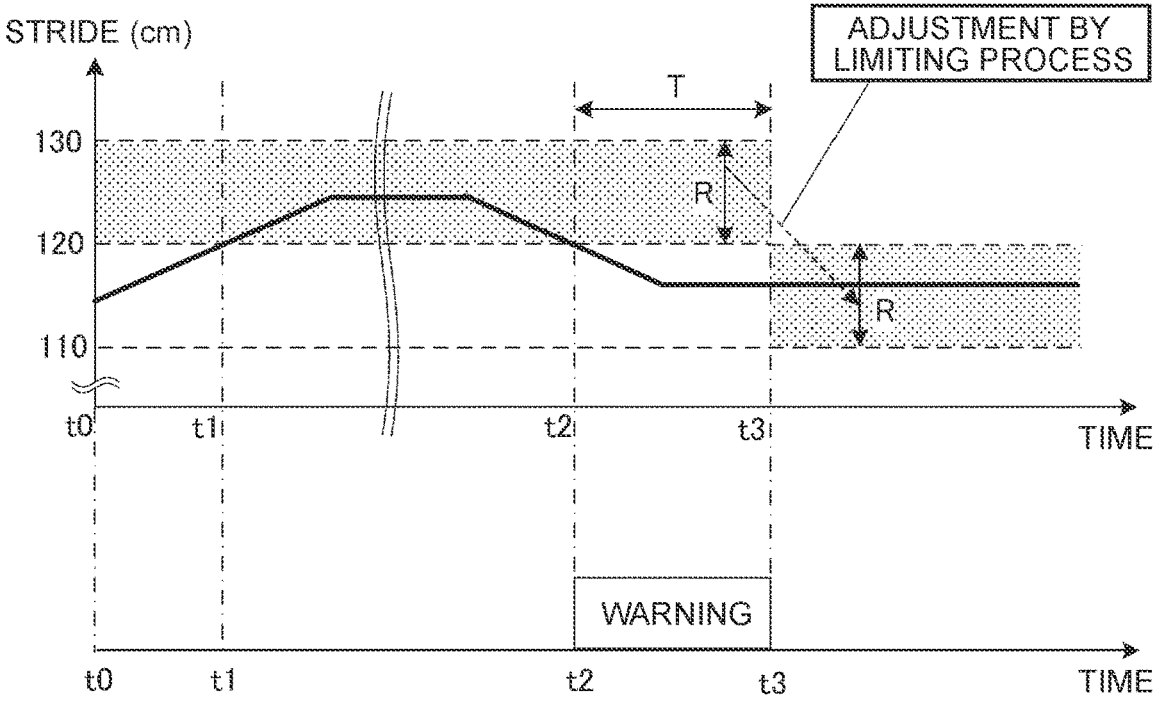
FIG. 4 is a diagram for describing the outline of an operation related to a warning function of the terminal device.

FIG. 4 is a diagram for describing the outline of the operation related to the warning function of the terminal device 10.

The graph in the upper part of FIG. 4 illustrates an example of a change over time in the size of the stride derived by the sensor device 20 after the start of running. It is assumed here that the running started at time to. The lower part of FIG. 4 illustrates the period during which the warning is given by the warning unit 14.

As illustrated in the graph in the upper part of FIG. 4, after the start of running at the time t0, the stride size increases to 120 cm or more at time t1 to fall within the normal range R, and subsequently the stride size is maintained within the normal range R until time t2. After the time t2, the stride size decreases to less than 120 cm and is out of the normal range R. The warning by the warning unit 14 starts at the time t2, in response to the fact that the stride size deviates from the normal range R. Alternatively, after the determination that the stride size deviates from the normal range R, the determination of whether the stride size is out of the normal range R is repeated at a predetermined cycle. Then, in the case where the stride size is out of the normal range R in a predetermined number of consecutive determinations, the warning may be started. This prevents the occurrence of a problem of hunting in the occurrence and stop of the warning.

After the warning is started, the warning is stopped in the case where the stride size falls within the normal range R. In this case, after the stride size is determined to fall within the normal range R, it may be repeated in a predetermined cycle to determine whether the stride size is within the normal range R. Then, when the stride size is within the normal range R in a predetermined number of consecutive determinations, the warning may be stopped. This prevents the occurrence of the problem of hunting in the occurrence and stop of the warning.

Hysteresis may be set for the values of the upper and lower limits of the normal range R. Specifically, the upper limit set value in the case of determining whether the stride size falls within the normal range R from outside the normal range R may be smaller than the upper limit set value in the case of determining whether the stride size deviates from the normal range R from within the normal range R. Moreover, the lower limit set value in the case of determining whether the stride size falls within the normal range R from outside the normal range R may be greater than the lower limit set value in the case of determining whether the stride size deviates from the normal range R from within the normal range R.

In the following, the function that generates a warning according to the set normal range R is referred to as "normal warning function." In the case where the normal range R is adjusted as described later, the "normal warning function" is a function that generates a warning according to the adjusted normal range R. In addition, the length of a time period during which a warning is generated by the normal warning function is denoted by "time T." The warning does not have to be in the mode of continuous display by the display unit 141, audio output by the audio output unit 142, or vibration by the vibration unit 143 over time T, but at least a part of the above display, audio output, and vibration may be generated intermittently at prescribed intervals over time T.

In this embodiment, no warning is given even if the stride size is out of the normal range R during the period since running starts at the time t0 until the stride size first falls within the normal range R (the period from the time t0 to the time t1 in FIG. 4). This is because the form is often unstable immediately after the start of running and it may be troublesome in some cases for the user U that the warning is given strictly on the basis of the set normal range R. When, however, the stride size has never been within the normal range R even after a predetermined suspended term (for example, 10 min) has passed since the start of running, the warning may be started. In an exercise in which a certain action is repeated, such as running, the warning may be started in the case where the stride size has never been within the normal range R even at the time when the number of times the above certain action is repeated (in running, for example, a value obtained by multiplying the pitch [the number of steps per unit time] by the time, or the number of steps) reaches a predetermined value since the start of exercise. It may also be possible to set the warning function to be performed immediately after the start of running.

In the case where the fatigue level of the user U in running increases, it may be difficult for the user U to keep the stride within the normal range R. Moreover, the running of the user U may have unpredictable waves of good and bad running. In the case of bad running, it may be difficult for the user U to keep the stride within the normal range R even if his/her fatigue level is not high. In addition, it may be difficult to keep the stride within the normal range R due to factors related to the environment around the user U, such as when running side by side with another runner who has a different running skill or when approaching a road surface in poor condition. In such cases, it is troublesome for the user U that the normal warning function continues to generate warnings in response to the fact that the stride is out of the normal range R.

Therefore, in this embodiment, it is determined whether an execution condition is satisfied, the execution condition including at least one of the following conditions: a first condition related to the length of time T during which a warning is generated by a normal warning function; a second condition related to the fatigue level of the user U; a third condition that the content of the exercise being performed by the user U is not a certain content; a fourth condition related to the possibility of achieving the goal related to the exercise of the user U; and a fifth condition related to an athletic ability of the user U. Then, on the condition that the execution condition is satisfied, a limiting process is performed to control the warning function so that the warning is more limited than in the case of the normal warning function. The limiting process in this embodiment includes the process of adjusting the normal range R so that warnings are less likely to be generated than in the case of the normal warning function (hereinafter, also simply referred to as "adjusting the normal range R"), and the process of stopping the warning of the warning function. In the example illustrated in FIG. 4, the lower and upper limits of the normal range R are reduced to 110 cm and 120 cm, respectively, at time t3 as the limiting process. As a result, after the time t3, the stride size of the user U falls within the normal range R, and the warning by the warning unit 14 stops. The normal range R may be adjusted so that the stride at the time when the limiting process is performed falls within the adjusted normal range R, or the upper and lower limits may be reduced by a predetermined adjustment range. It is acceptable to expand the normal range R by reducing only the lower limit of the normal range R. It is also acceptable to expand the normal range R by decreasing the lower limit and increasing the upper limit.

When the normal range R is adjusted, the "normal warning function" is set to generate a warning according to the adjusted normal range R. Therefore, when the above-mentioned execution condition is satisfied for the normal warning function started after the adjustment of the normal range R, the limiting process may be performed again. Thus, the normal range R may be adjusted more than once. In the second and subsequent adjustments of the normal range R, the normal range R is adjusted so that the range is less likely to cause a warning than the normal range R immediately before the limiting process for the adjustment of the normal range R is performed (in the example in FIG. 4, so that the upper and lower limits are reduced from those of the immediately preceding normal range R).

In this embodiment, a reference number of times to adjust the normal range R is set in advance. When the number of times the normal range R is adjusted after the start of running is less than the reference number of times, the normal range R is adjusted in the limiting process performed in the case where the execution condition is satisfied next time. When the limiting process has already been performed a reference number of times after the start of running, the warning is stopped by the warning function in the limiting process performed in the case where the execution condition is satisfied next time. After the warning by the warning function is stopped, the warning unit 14 does not generate a warning even if the stride of the user U is out of the normal range R.

The following is a detailed description of the execution condition of the limiting process.

The execution condition may be satisfied when at least one of the first to fifth conditions is satisfied. For example, the execution condition may be satisfied when arbitrary one of the first to fifth conditions is satisfied. In addition, the execution condition may be satisfied when a predetermined number or more of arbitrary conditions of the first to fifth conditions are satisfied. Moreover, the execution condition may also be satisfied when at least one specific condition or a combination of specific two or more of the first to fifth conditions is satisfied. For example, the execution condition may be satisfied when at least the first condition is satisfied. The execution condition may be satisfied when both of the first and second conditions are satisfied.

The first condition, which is one of the determination targets in the execution condition, is conditional on that the duration of the warning generated by the normal warning function (time T in FIG. 4) has reached the predetermined determination time. In this embodiment, "a certain condition is conditional on the occurrence of a certain event" may be replaced by "a certain condition is satisfied when a certain event occurs." In the case of an exercise in which a certain action is repeated, such as running, it may be determined that the duration of the warning state has reached the determination time on the basis of a fact that the number of times the certain action described above is repeated (in running, for example, a value obtained by multiplying the pitch by time, or the number of steps) after the start of the warning reaches a predetermined value corresponding to the determination time.

The first condition may also be conditional on that the total time of the state, in which a warning is generated by the normal warning function during a certain period of time, has reached the determination time. In other words, the first condition may be satisfied when the warning by the normal warning function is intermittently performed for a plurality of periods within a certain period of time, and when the total time, which is the sum of the lengths of the plurality of periods within a certain period of time, reaches the determination time. The above "certain period" is a period slightly longer than the determination time. For example, when the determination time is 20 minutes, the above certain period may be about 10% (two minutes) longer than the determination time.

The determination time may be changed according to the situation of running. For example, the period during which the fatigue level tends to increase may be defined as a condition relaxation period for the first condition. Then, in the condition relaxation period, the determination time may be shorter than the period other than the condition relaxation period (hereinafter, referred to as "normal period"), thereby relaxing the execution condition of the limiting process. In this embodiment, the total section of the running course (for example, the section of 42.195 km in the case of a marathon) is divided into the first half and the second half. Then, the determination time is set to 20 minutes in the normal period during which a runner runs in the first half, and the determination time is reduced to 10 minutes with the period during which the runner runs in the second half as the condition relaxation period. The condition relaxation period is not limited to the period corresponding to the latter half of the all sections of the course, but may be, for example, the period corresponding to the section of the last predetermined distance (for example, the last 10 km, or the like) of all sections of the course, for example. In addition, continuous two or more condition relaxation periods may be defined and then the execution condition may be relaxed in a plurality of steps so that the later the condition relaxation period is, the shorter the determination time is.

In addition, the above settings of the determination time for the normal period and for the condition relaxation period may be changed to a longer time than the normal period in the case where the heart rate, which is the biometric information representing the height of the fatigue level of the user U, is less than the first threshold value (for example, less than 176 [bpm]) (in other words, the determination time may be increased by the adjustment). In this embodiment, when the heart rate is less than the first threshold value, the determination time is set to 30 minutes, assuming that the fatigue level of the user U is not so high and that the user U is running comfortably. On the other hand, when the heart rate is equal to or higher than the first threshold value, the above determination time for the normal period (20 minutes) or the determination time for the condition relaxation period (10 minutes) is applied, assuming that the fatigue level of the user U is high and that the user U is running uncomfortably.

The above settings of the determination time for the normal period and for the condition relaxation period may be changed to a longer time than the normal period when the pace of the running of the user U (the value corresponding to the moving speed) is equal to the second threshold value (for example, 5 [min/km]) or faster than the second threshold value. In this embodiment, when the pace is equal to the second threshold value or faster than the second threshold value, the determination time is set to 30 minutes, assuming that the fatigue level of the user U is not so high and that the user U is running comfortably. On the other hand, when the pace is slower than the second threshold value, the determination time for the normal period (20 minutes) or the determination time for the condition relaxation period (10 minutes) is applied, assuming that the fatigue level of the user U is high and that the user U is running uncomfortably or that the situation around the user U makes it difficult to increase the pace.

The above settings of the determination time for the normal period and for the condition relaxation period may be changed to a time longer than the normal period when the value representing the possibility of achieving the goal for the running of the user U is equal to or greater than the predetermined third threshold value. The goal may be that the user U moves a certain distance within a reference time in the exercise, in the case where the exercise of the user U involves the movement of the user U. The exercise of this embodiment is to run a distance set at the start of the exercise (running), and the goal is to complete a predetermined set distance within the reference time set at the start of the exercise. The possibility of achieving the goal is derived based on the history of the moving speed of the running user U. For example, based on the history of the moving speed of the running user U up to a certain time point, the time to complete the set distance is predicted, and a value representing the possibility of achieving the goal is derived based on the relationship between the predicted time and the reference time. Moreover, it is determined that the shorter the predicted time is, the higher the possibility of achieving the goal is. The time for the user U to complete the set distance may be derived by using a learning model machine-learned to take the history of the moving speed of the user U up to a certain time point as an input and to output the estimated time for the user U to complete the set distance. The learning model may also be one to directly derive a value representing the possibility of achieving the goal.

In this embodiment, the user U is assumed to be highly motivated to perform exercise for achieving the goal when the value representing the possibility of achieving the goal is equal to or greater than the third threshold value, and the determination time is set to 60 minutes so that the warning is given over the required time. On the other hand, when the value representing the possibility of achieving the goal is less than the third threshold value, the above determination time for the normal period (20 minutes) or the determination time for the condition relaxation period (10 minutes) is applied, assuming that the user U is likely to be in a condition where he/she cannot achieve the goal and that the user U is running uncomfortably or that the situation is difficult for the user U to run.

The determination time may be set based on the athletic ability information that represents the athletic ability of the user U. For example, the determination time may be set so that the higher the athletic ability of the user U represented by the athletic ability information is, the longer the determination time is. In this embodiment, the time of the user U to complete a full marathon (the best time) is used as the athletic ability information. When the full marathon completion time is less than three hours and 30 minutes, the user U is determined to have high athletic ability, and the determination time is set to 60 minutes.

The second condition, which is one of the determination targets in the execution condition, is determined based on the biometric information of the user U during running. In this embodiment, the heart rate derived from the detection result of the pulse wave detection unit 16 of the terminal device 10 is used as the biometric information. The second condition is conditional on that the heart rate of the user U is equal to or greater than the first threshold value described above. When the heart rate is equal to or higher than the first threshold value, the fatigue level of the user U is able to be assumed to be high. In other words, it can be assumed that the user U is running uncomfortably due to the high fatigue level, and that the user U is in a state where it is not easy to return the warning target index (in this embodiment, the stride) to the normal range R in response to a warning. Therefore, when the second condition is satisfied, it is preferable to perform a limiting process of limiting the warning, which is generated by the warning unit 14, for the user U.

The fatigue level of the user U may be determined based on the self-reported content of the user U. For example, at the start of running, a dialog screen for inputting the fatigue level of the user U may be displayed on the exercise application 131, and the fatigue level may be determined based on the content that the user U inputs on the dialog screen. As the mode for inputting the fatigue level by the user U, the user U may select one of two levels such as, for example, "(the fatigue level is) high or not high," of three levels such as "(the fatigue level is) high, normal, or low," or of four or more levels. Moreover, the user may also directly input a value representing the fatigue level.

The fatigue level of the user U includes the physical condition of the user U. When the user U is in poor physical condition, it corresponds to a fact that the fatigue level of the user U is high. For example, the above dialog screen may be a screen for inputting the physical condition as a fatigue level. As the mode for inputting the physical condition, the user may select one of two levels such as "(the physical condition is) bad or good," of three levels such as "(the physical level is) bad, normal, or good," or of four or more levels. The user may also directly input a value representing his/her physical condition.

The self-reporting of the fatigue level or the physical condition by the user U may be able to be performed during running.

The third condition is satisfied when the content of running is not a certain content. In this embodiment, when the pace of the user U in running is slower than the second threshold value, then the content of the running is determined to be not the above certain content. When the pace of the user U is slower than the second threshold value, it can be assumed that the user U is in a state where it is difficult for the user U to return the warning target index (in this embodiment, stride) to the normal range R in response to a warning for some reason, such as fatigue or surrounding conditions. Therefore, when the third condition is satisfied, it is preferable to perform a limiting process of limiting the warning, which is generated by the warning unit 14, for the user U.

The fourth condition is satisfied when the value representing the possibility of achieving the goal for running of the user U is less than the predetermined third threshold value, as described above. When the value representing the possibility of achieving the goal is less than the third threshold value, there is a high possibility that the user U is in a condition where he/she cannot achieve the goal, and it can be assumed that, for some reason, it is difficult to improve the exercise state to a state where no warning is given. Therefore, when the fourth condition is satisfied, it is preferable to reduce the annoyance of warnings by limiting the warnings for the user U, rather than continuing to generate the warnings as configured.

On the other hand, when the value representing the possibility of achieving the goal is equal to or greater than the third threshold value, the user U can be assumed to be highly motivated to exercise for achieving the goal. Therefore, unless the fourth condition is satisfied, it is preferable to generate a warning as configured for the user U.

The fifth condition is satisfied when the athletic ability of the user U, which is represented by the above-mentioned athletic ability information, does not meet a given criterion. In this embodiment, the criterion for the athletic ability is that the full marathon completion time is less than three hours and 30 minutes. Unless the athletic ability of the user U meets the above criterion, it can be assumed that the user U has difficulty in returning the warning target index (in this embodiment, stride) to the normal range R, from the viewpoint of athletic ability. Therefore, when the fifth condition is satisfied, it is preferable to perform a limiting process of limiting the warning, which is generated by the warning unit 14, for the user U.

The warning by the warning unit 14 and the limiting process of limiting the warning described above are performed based on the warning setting data 132 stored in the memory 13 of the terminal device 10.

FIG. 5 is a diagram illustrating an example of the contents of the warning setting data 132.

Hereinafter, respective data items included in the warning setting data 132 are described. The value of each data item may be able to be set by the user U on the exercise application 131 to a desired content or value. In addition, the value of each data item may be set by the CPU 11 on the basis of the information on the attributes and characteristics of the user U, the information on the history of the exercise of the user U, or the like.

The warning setting data 132 includes "data related to the warning target index" and "data related to the execution condition of the limiting process." The "data related to the warning target index" includes the following data items: "warning target index," "initial upper limit of the normal range," "initial lower limit of the normal range," "adjusted upper limit of the normal range," and "adjusted lower limit of the normal range." The "data related to the execution condition of the limiting process" includes the following data items: "determination time," "first threshold value for pulse rate determination," "second threshold value for pace determination," "third threshold value for possibility of achieving a goal," "full marathon completion time," and "reference number of times for normal range adjustment."

The "warning target index," which is an index related to the exercise that is a target of warning generated by the warning unit 14 as described above, is a stride in this embodiment.

The "initial upper limit of the normal range" and the "initial lower limit of the normal range" represent the upper and lower limits of the initial normal range R before being limited by the limiting process. These upper and lower limits are referenced to determine whether to perform warning of the normal warning function before the first limiting process is performed.

The "adjusted upper limit of the normal range" and the "adjusted lower limit of the normal range" are set when the normal range R has been adjusted by at least one limiting process. The "adjusted upper limit of the normal range" and the "adjusted lower limit of the normal range" represent the (latest) upper and lower limits of the normal range R adjusted by the last limiting process, and are referenced to determine whether to perform warning of the normal warning function after the limiting process has been performed.

In the data items of "determination time," there are set the values for the determination time such as "value for normal period," "value for condition relaxation period," a value for the "low fatigue or high pace period," and a value for the "case of high possibility of achieving the goal or high athletic ability." Among them, the value for the "low fatigue or high pace period" represents the determination time applied in the case where the heart rate is equal to or higher than the second threshold value, and in the case where the pace is equal to the second threshold value or faster than the second threshold value. Moreover, the value for the "case of high possibility of achieving the goal or high athletic ability" represents the determination time applied when the value representing the possibility of achieving the goal of running is equal to or higher than the third threshold value and when the full marathon completion time is less than three hours and 30 minutes.

The "first threshold value for pulse rate determination" is the above-mentioned first threshold value used to set the determination time or to determine the second condition.

The "second threshold value for pace determination" is the above-mentioned second threshold value used to set the determination time and to determine the third condition.

The "third threshold value for possibility of achieving a goal" is the above-mentioned third threshold value used to determine the fourth condition. The third threshold value may be used to set the determination time.

The "full marathon completion time" is the time recorded at which the user U has finished the full marathon, which is used for setting the determination time and for determining the fifth condition. The "full marathon completion time" corresponds to the athletic ability information representing the athletic ability of the user U.

The "reference number of times of normal range adjustment" is the above-mentioned reference number of times for adjusting the normal range R.

<Processing for Warning Operation>

Subsequently, description is made on a control procedure for a warning process performed by the CPU 11 of the terminal device 10 to perform the operation for the above-mentioned warning function and the operation of limiting the warning function, with reference to the flowcharts of FIG. 6 and FIG. 7.

Figure 6:
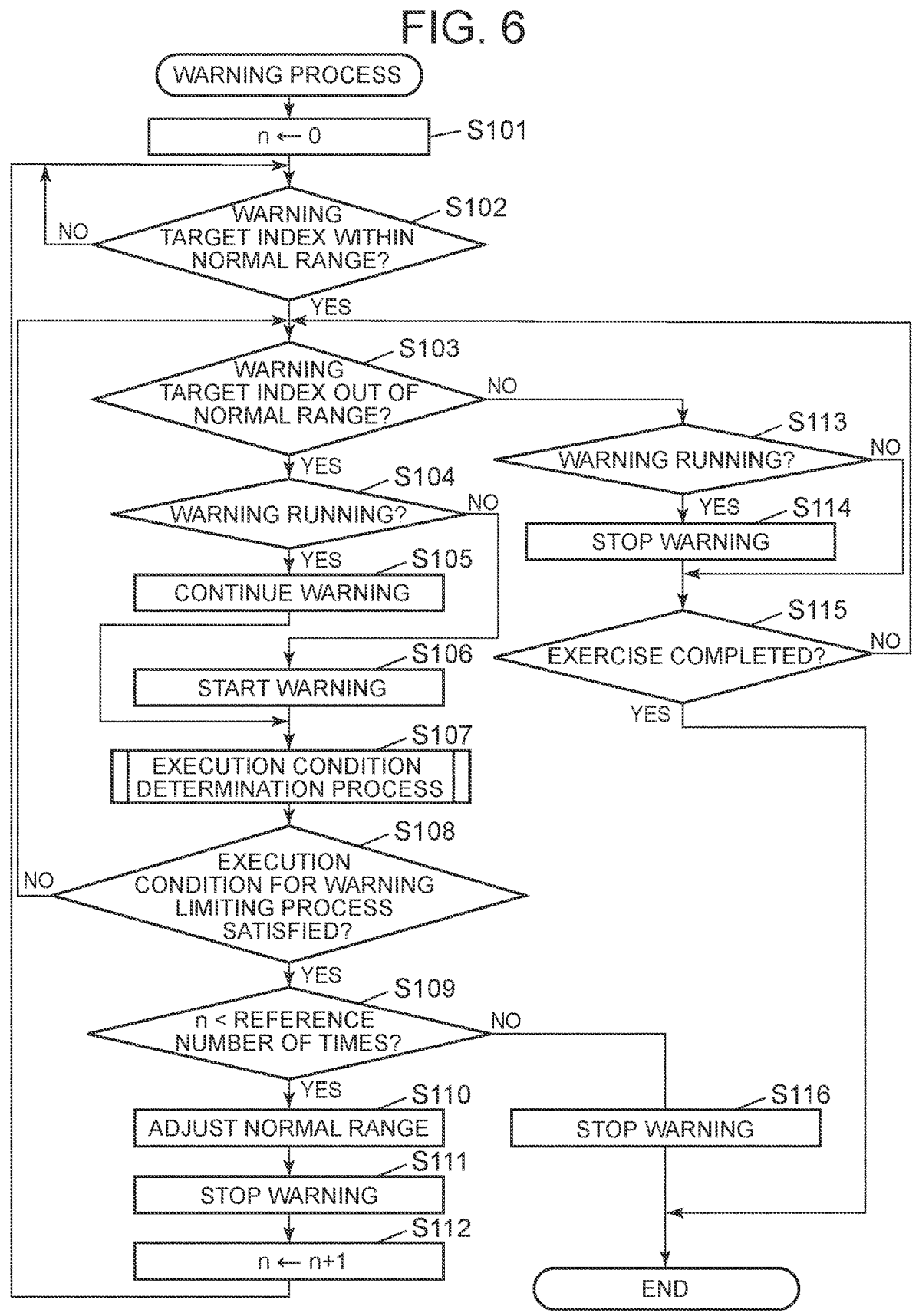
FIG. 6 is a flowchart illustrating a control procedure for a warning process.

FIG. 6 is a flowchart illustrating the control procedure for the warning process.

The warning process is initiated when the exercise of the user U is started. The start of the exercise of the user U may be determined, for example, based on a fact that the user U has performed a predetermined operation representing the start of the exercise on the exercise application 131, or may be determined based on a fact that the terminal device 10 has received a notification from the sensor device 20 that detected the start of the exercise. During the exercise being performed, the exercise data including information on the exercise state of the user U is continuously sent from the sensor device 20 to the terminal device 10.

When the warning process is started, the CPU 11 assigns "0" to a variable n that represents the number of times the normal range R is adjusted after the start of the exercise (step S101).

The CPU 11 determines whether the value of the warning target index included in the latest exercise data received from the sensor device 20 is within the normal range R (step S102). In this specification, when the value of the warning target index is equal to or less than the "initial upper limit of the normal range" and equal to or greater than the "initial lower limit of the normal range" in the warning setting data 132, the CPU 11 determines that the value of the warning target index is within the normal range R. When the value of the warning target index is determined not to be within the normal range R ("NO" in step S102), the CPU 11 performs step S102 again without giving a warning. This is because the form is often unstable immediately after the start of running, and it may be troublesome for the user U that the warning is given strictly based on the preset normal range R.

Note that, in the case of performing step S102 at least once after the adjustment of the normal range R in step S110 described later, the CPU 11 determines that the value of the warning target index is within the normal range R when the value of the warning target index is equal to or less than the "adjusted upper limit of the normal range" and equal to or greater than the "adjusted lower limit of the normal range" in the warning setting data 132.

When the value of the warning target index is determined to be within the normal range R ("YES" in step S102), the CPU 11 determines whether the value of the warning target index included in the latest exercise data received from the sensor device 20 is out of the normal range R (step S103). When the variable n is "0," in other words, when the normal range R has not been adjusted yet, the CPU 11 determines that the value of the warning target index is out of the normal range R in the case where the value of the warning target index is greater than the "initial upper limit of the normal range" or less than the "initial lower limit of the normal range" in the warning setting data 132. Moreover, when the variable n is "1" or greater, in other words, when the normal range R has been adjusted at least once, the CPU 11 determines that the value of the warning target index is out of the normal range R in the case where the value of the warning target index is greater than the "adjusted upper limit of the normal range" or less than the "adjusted lower limit of the normal range" in the warning setting data 132.

When the value of the warning target index is not out of the normal range R (is within the normal range R) ("NO" in step S103), the CPU 11 determines whether warning by the warning unit 14 is running (step S113). When it is determined that the warning is running ("YES" in step S113), the CPU 11 outputs a control signal to the warning unit 14 to stop the warning (step S114). When step S114 is completed or when it is determined that the warning is not running in step S113 ("NO" in step S113), the CPU 11 determines whether the exercise of the user U is completed (step S115). The completion of the exercise of the user U may be determined, for example, based on a fact that the user U has performed a predetermined operation representing the completion of the exercise on the exercise application 131 or may be determined based on a fact that a notification is received from the sensor device 20 that has detected the completion of the exercise. When it is determined that the exercise of the user U is not completed ("NO" in step S115), the CPU 11 returns the process to step S103.

When it is determined that the value of the warning target index is out of the normal range R ("YES" in step S103), the CPU 11 determines whether the warning by the warning unit 14 is running (step S104). When it is determined that the warning is running ("YES" in step S104), the CPU 11 outputs a control signal to the warning unit 14 to continue the warning (step S105). When it is determined that the warning is not running ("NO" in step S104), the CPU 11 outputs a control signal to the warning unit 14 to start the warning (step S106). This warning is continued until the warning is stopped in step S111 or step S116 described later.

The CPU 11 performs the execution condition determination process (step S107) to determine whether to perform the limiting process of limiting the warning in progress. As described later, the execution condition determination process results in either determination of "execution condition satisfied" or "execution condition not satisfied."

The CPU 11 determines whether the result of the determination in the execution condition determination process is "execution condition satisfied" (step S108). When the determination result is "execution condition not satisfied" ("NO" in step S108), the CPU 11 returns the process to step S103. When the execution condition is determined to be not satisfied, the execution condition determination process of step S107 is performed again, as long as the warning target index is out of the normal range ("YES" in step S103 and "YES" in step S104).

When the determination result is "execution condition satisfied" ("YES" in step S108), the CPU 11 determines whether the variable n is less than the "reference number of times for normal range adjustment" set in the warning setting data 132 (step S109). When the variable n is determined to be less than the "reference number of times for normal range adjustment" ("YES" in step S109), the CPU 11 adjusts the upper and lower limits of the normal range R as described above and stores the adjusted values as "adjusted upper limit of the normal range" and "adjusted lower limit of the normal range" in the warning setting data 132 (step S110).

When step S110 is completed, the CPU 11 outputs a control signal to the warning unit 14 to stop the warning (step S111). The CPU 11 also assigns "n+1" to the variable n (step S112) and returns the process to step S102. Therefore, when the normal range R is adjusted in step S110 and the warning is stopped in step S111, thereafter the normal warning function does not resume and the next warning (step S106) is not started, until the warning target index falls within the adjusted normal range R ("YES" in step S102).

On the other hand, when the variable n is determined to be equal to the "reference number of times for normal range adjustment" in step S109 ("NO" in step S109), the CPU 11 outputs a control signal to the warning unit 14 to stop the warning (step S116). When the warning is stopped in step S116, no further warning is given thereafter until the completion of the exercise. In other words, when the number of times the limiting process (in this case, the process of adjusting the normal range R in step S110 and stopping the warning in step S111) has been performed reaches the prohibited number of times equal to or more than the reference number of times, subsequent warnings are prohibited regardless of the relationship between the warning target index and the normal range R.

When step S116 is completed, or when it is determined that the exercise of the user U is completed in step S115 ("YES" in step S115), the CPU 11 terminates the warning process.

Among the above warning processes, the process of adjusting the normal range R in step S110 and stopping the warning in step S111 corresponds to the limiting process. Moreover, the process of stopping the warning in step S116 corresponds to the limiting process.

The above is an example of the control procedure for the warning process, and may be appropriately changed according to the settings or the like made on the exercise application 131.

For example, after the warning is stopped in step S111 and the variable n is incremented in step S112, the process may be returned to step S103. In other words, after the warning is stopped in step S111, the normal warning function may be resumed regardless of whether the warning target index falls within the normal range R. In this case, the variable n may be the number of consecutive times the limiting process is performed during the period in which the warning target index remains out of the normal range R. In other words, the variable n may be reset to "0" when the warning target index falls within the normal range R ("NO" in step S103).

Moreover, in the mode for returning the process from step S112 to step S103, the process of stopping the warning in step S111 may be omitted. When the process is done in this way, in the case where the warning target index does not fall within the normal range R even by adjusting the normal range R in step S110, the process branches to "YES" in step S103, and then to "YES" in step S104, by which the warning is continued (step S105). In this case, the start point of warning by the normal warning function may be the point when step S105 (continuation of warning) is performed.

Figure 7:
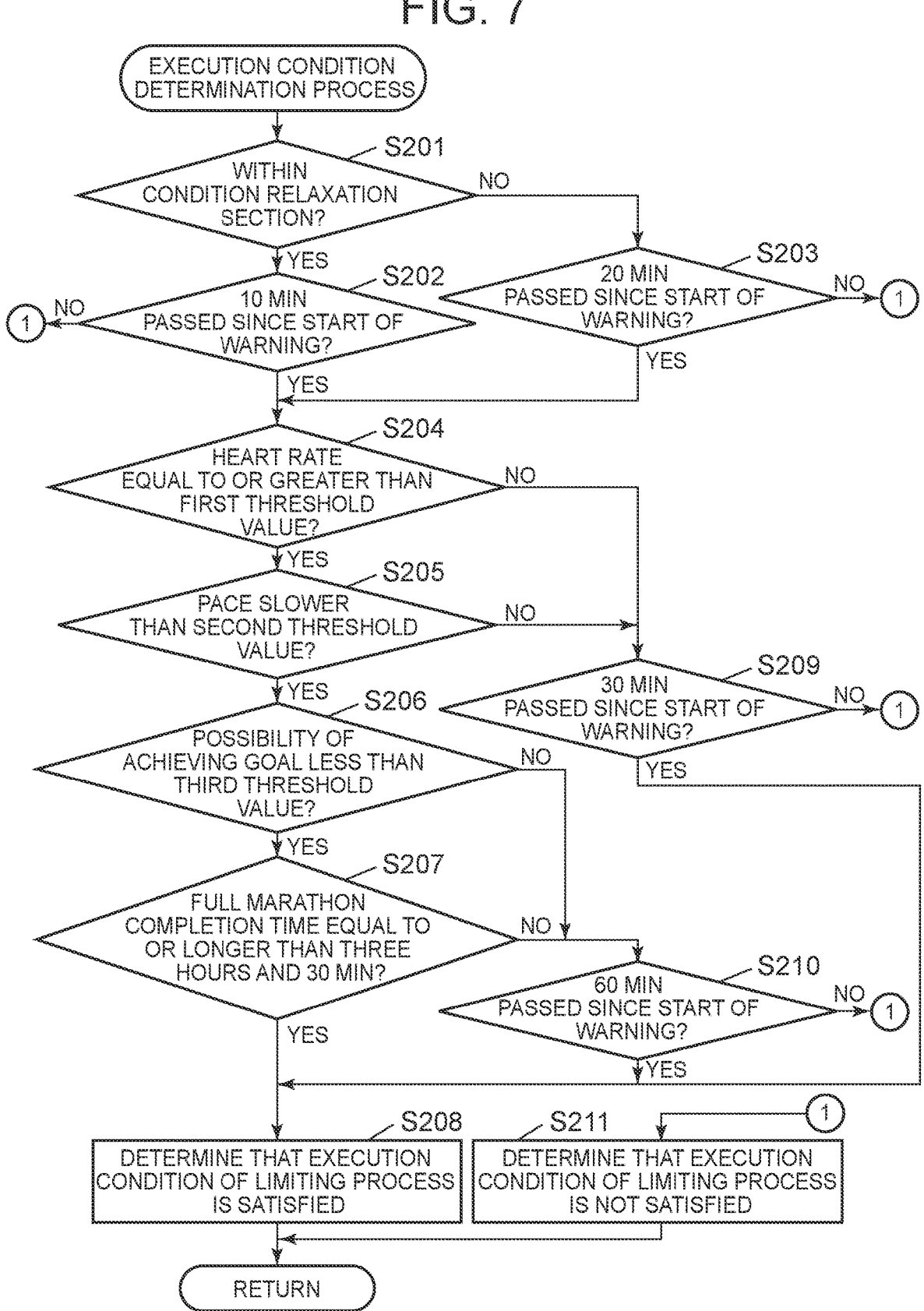
FIG. 7 is a flowchart illustrating a control procedure for an execution condition determination process.

FIG. 7 is a flowchart illustrating a control procedure for an execution condition determination process.

When the execution condition determination process is called, the CPU 11 determines whether the position of the user U at that time point in all sections of the exercise (running) is within the condition relaxation section in the latter half of the exercise (step S201). In this specification, the CPU 11 acquires the moving distance of the user U in the current exercise from the exercise data received from the sensor device 20, and determines whether the position of the user U is within the condition relaxation section on the basis of the moving distance and of the set distance and the condition relaxation section, which are predetermined for the current exercise.

When the position of the user U is determined to be within the condition relaxation section ("YES" in step S201), the CPU 11 refers to the warning setting data 132 to acquire the determination time in the condition relaxation period. Then, after the warning by the normal warning function is started (in the example in FIG. 6, after the warning is started in step S106), the CPU 11 determines whether the duration of the warning state has reached the determination time (in this case, 10 minutes) (whether the determination time has passed since the start of the warning) (step S202). On the other hand, when the position of the user U is determined to be not within the condition relaxation section ("NO" in step S201), the CPU 11 refers to the warning setting data 132 to acquire the determination time in the normal period, and determines whether the duration of the warning state has reached the determination time (in this case, 20 minutes) (whether the determination time has passed since the start of the warning) (step S203).

Note that whether the position of the user U is within the condition relaxation section may not be considered. In that case, steps S201 and S202 are omitted and step S203 is performed to determine whether the determination time in the normal period has passed.

When it is determined in step S202 that 10 minutes have not passed since the start of the warning ("NO" in step S202), or when it is determined in step S203 that 20 minutes have not passed since the start of the warning ("NO" in step S203), the CPU 11 determines that the execution condition of the limiting process is not satisfied (step S211).

When it is determined in step S202 that 10 minutes have passed since the start of the warning ("YES" in step S202), or when it is determined in step S203 that 20 minutes have passed since the start of the warning ("YES" in step S203), the CPU 11 derives the heart rate on the basis of the detection result of the pulse wave detection unit 16, and determines whether the heart rate is equal to or greater than the first threshold value, which is set in the warning setting data 132 (step S204).

When the heart rate is determined to be equal to or greater than the first threshold value ("YES" in step S204), the CPU 11 determines whether the pace of the user U in the latest exercise data received from the sensor device 20 is slower than the second threshold value set in the warning setting data 132 (step S205).

When the pace of the user U is determined to be slower than the second threshold value ("YES" in step S205), the CPU 11 derives a value representing the possibility of achieving the goal of the exercise on the basis of the history of the moving speed of the user U, and determines whether the value is less than the third threshold value set in the warning setting data 132 (step S206).

When the value representing the possibility of achieving the goal of the exercise is determined to be less than the third threshold value ("YES" in step S206), the CPU 11 determines whether the full marathon completion time of the user U registered in the warning setting data 132 is equal to or longer than three hours and 30 minutes (step S207). When the full marathon completion time is determined to be equal to or longer than three hours and 30 minutes ("YES" in step S207), the CPU 11 determines that the execution condition of the limiting process is satisfied (step S208).

When the heart rate is determined to be less than the first threshold value in step S204 ("NO" in step S204) or when the pace of the user U is determined to be equal to the second threshold value or to be faster than the second threshold value in step S205 ("NO" in step S205), the CPU 11 refers to the warning setting data 132 to acquire the determination time for the "low fatigue or high pace period," and then determines whether the duration of the warning state has reached the determination time (in this case, 30 minutes) (whether the determination time has passed since the start of the warning) (step S209). When it is determined that 30 minutes have passed since the start of the warning ("YES" in step S209), the CPU 11 moves the process to step S208 and determines that the execution condition of the limiting process is satisfied. Unless it is determined that 30 minutes have passed since the start of the warning ("NO" in step S209), the CPU 11 moves the process to step S211 to determine that the execution condition of the limiting process is not satisfied.

When the value representing the possibility of achieving the goal of the exercise is determined to be equal to or greater than the third threshold value in step S206 ("NO" in step S206), or when the full marathon completion time is determined to be less than three hours and 30 minutes in step S207 ("NO" in step S207), the CPU 11 refers to the warning setting data 132 to acquire the determination time for the "case of high possibility of achieving the goal or high athletic ability" and determines whether the duration of the warning state has reached the concerned determination time (in this case, 60 minutes) (whether the concerned determination time has passed since the start of the warning) (step S210). When it is determined that 60 minutes have passed since the start of the warning ("YES" in step S210), the CPU 11 moves the process to step S208 and determines that the execution condition of the limiting process is satisfied. When it is determined that 60 minutes have not passed since the start of the warning ("NO" in step S210), the CPU 11 moves the process to step S211 and determines that the execution condition of the limiting process is not satisfied.

Upon the completion of step S208 or step S211, the CPU 11 terminates the execution condition determination process and returns the process to the warning process.

In the execution condition determination process illustrated in FIG. 7, steps S201 to S203, S209, and S210 correspond to the processes of determining whether the first condition is satisfied. Step S204 corresponds to the process of determining whether the second condition is satisfied.

Moreover, step S205 corresponds to the process of determining whether the third condition is satisfied. Step S206 corresponds to the process of determining whether the fourth condition is satisfied. Step S207 corresponds to the process of determining whether the fifth condition is satisfied.

In the execution condition determination process illustrated in FIG. 7, the condition for the execution condition to be satisfied is that at least the first condition is satisfied. In other words, the execution condition is determined to be satisfied by performing step S208 only when at least one of steps S202, S203, S209, and S210, which are related to the determination of the first condition, results in a "YES" branch. Thus, the execution condition may be configured to be satisfied when at least the first condition is satisfied.

In FIG. 7, step S204, which is related to determining the second condition, may be omitted.

Step S205, which is related to determining the third condition, may also be omitted. When both steps S204 and S205 are omitted, step S209 is also omitted.

In addition, step S206, which is related to determining the fourth condition, may be omitted.

Step S207, which is related to determining the fifth condition, may be omitted. When both steps S206 and S207 are omitted, then step S210 is also omitted.

In addition, steps S209 and S210 may be omitted, with performing the determination related to the first condition only in steps S201 to S203. In this case, step S211 is performed when any of steps S204 to S207 results in a "NO" branch.

Any two or more of the above omission of step S204, omission of step S205, omission of step S206, omission of step S207, and omission of steps S209 and S210 may be combined.

<Variation>

Subsequently, variations of the above embodiments are described. In each variation, the differences from the above embodiments are described, and the description of points in common with the embodiments are omitted.

(Variation 1)

In this variation, the condition for the execution condition of the limiting process to be satisfied is that both the first and second conditions are satisfied.

Figure 8:
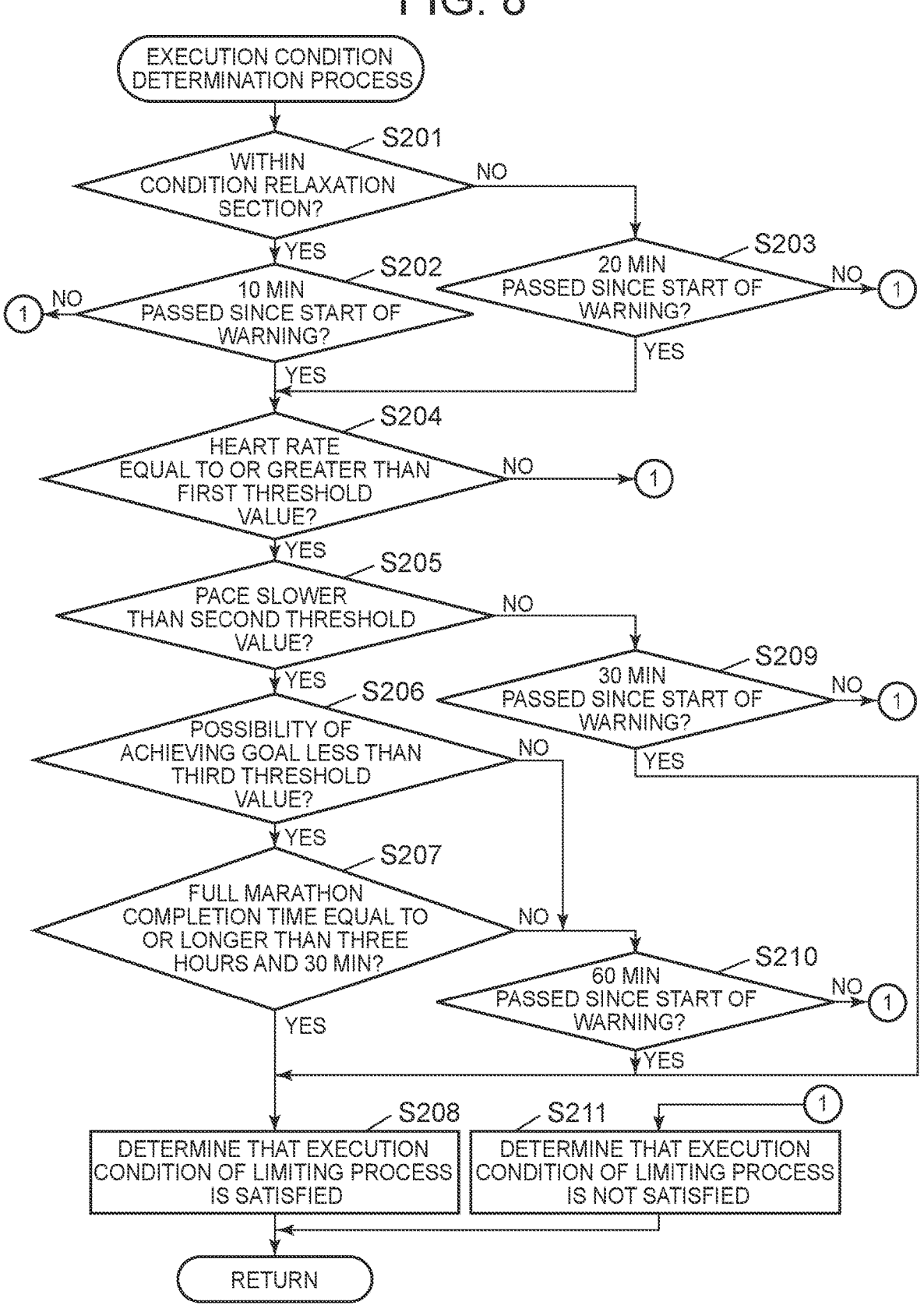
FIG. 8 is a flowchart illustrating a control procedure for an execution condition determination process according to variation 1.

FIG. 8 is a flowchart illustrating a control procedure for an execution condition determination process according to variation 1.

In the execution condition determination process illustrated in FIG. 8, when the heart rate is determined to be less than the first threshold value in step S204 ("NO" in step S204), the process is moved to step S211 and it is determined that the execution condition is not satisfied. Except for this point, the flowchart in FIG. 8 is identical to the flowchart in FIG. 7. According to the execution condition determination process illustrated in FIG. 8, only in the case where the first condition is determined to be satisfied in step S202 or S203 ("YES" in steps S202 or S203) and the second condition is determined to be satisfied in step S204 ("YES" in step S204), the process of step S208 (the process of determining that the execution condition is satisfied) is able to be performed.

In FIG. 8, step S205, which is related to determining the third condition, may be omitted. When step S205 is omitted, step S209 is also omitted.

Moreover, step S206, which is related to determining the fourth condition, may be omitted.

Step S207, which is related to determining the fifth condition, may be omitted. When both steps S206 and S207 are omitted, then step S210 is also omitted.

In addition, the determination related to the first condition may be performed only in steps S201 to S203, with steps S209 and S210 being omitted. In this case, step S211 is performed when any of steps S205 to S207 results in a "NO" branch.

Any two or more of the above omission of step S205, omission of step S206, omission of step S207, and omission of steps S209 and S210 may be combined.

(Variation 2)

In this variation, the condition for the execution condition of the limiting process to be satisfied is that at least the second condition is satisfied.

Figure 9:
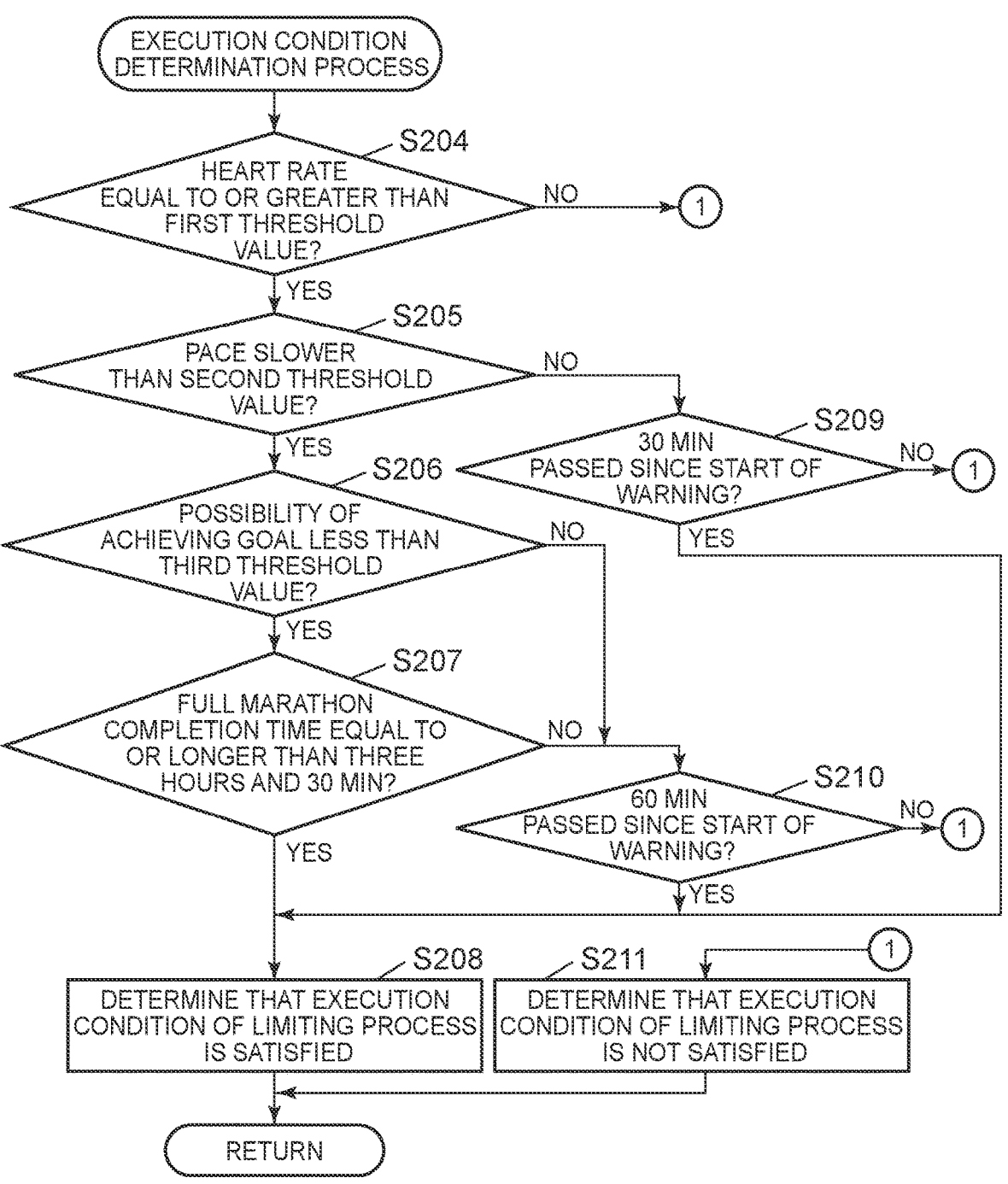
FIG. 9 is a flowchart illustrating a control procedure for an execution condition determination process according to variation 2.

FIG. 9 is a flowchart illustrating a control procedure for an execution condition determination process according to variation 2.

The flowchart in FIG. 9 corresponds to the flowchart in FIG. 8 without steps S201 to S203. According to the execution condition determination process illustrated in FIG. 9, the process of step S208 (the process of determining that the execution condition is satisfied) is able to be performed, only when the second condition is determined to be satisfied at least in step S204 ("YES" in step S204).

Note that, in FIG. 9, step S205, which is related to determining the third condition, may be omitted. When step S205 is omitted, step S209 is also omitted.

Step S206, which is related to determining the fourth condition, may also be omitted.

In addition, step S207, which is related to determining the fifth condition, may be omitted. When both steps S206 and S207 are omitted, step S210 is also omitted.

Steps S209 and S210 may also be omitted, without performing the determination related to the first condition (in other words, the satisfied first condition is not a requirement for the satisfied execution condition). In this case, step S211 is performed when any of steps S205 to S207 results in a "NO" branch.

In addition, any two or more of the above omission of step S205, omission of step S206, omission of step S207, and omission of steps S209 and S210 may be combined.

(Variation 3)

The execution condition of the limiting process may be configured to be satisfied on the condition that at least the third condition is satisfied. In this case, for example, when step S205 is performed before step S204 of the execution condition determination process illustrated in FIG. 9 and the pace of the user U is determined in this step S205 to be equal to the second threshold value or to be faster than the second threshold value ("NO" in step S205), the process is moved to step S211 to determine that the execution condition of the limiting process is not satisfied. When the pace of the user U is determined to be slower than the second threshold value in step S205 ("YES" in step S205), then step S204 is performed. When the heart rate is determined to be less than the first threshold value in this step S204 ("NO" in step S204), then step S209 may be performed instead of step S211.

In this variation, step S204, which is related to determining the second condition, may be omitted.

Moreover, step S206, which is related to determining the fourth condition, may be omitted.

Furthermore, step S207, which is related to determining the fifth condition, may be omitted. When both steps S206 and S207 are omitted, step S210 is also omitted.

In addition, steps S209 and S210 may be omitted, with step S211 being performed instead of steps S209 and S210 (in other words, the satisfied first condition may not be a requirement for the satisfied execution condition).

Furthermore, any two or more of the above omission of step S204, omission of step S206, omission of step S207, and omission of steps S209 and S210 may be combined.

(Variation 4)

The execution condition of the limiting process may be configured to be satisfied on the condition that at least the fourth condition is satisfied. In this case, for example, when step S206 is performed before step S204 of the execution condition determination process illustrated in FIG. 9 and the value representing the possibility of achieving the goal of exercise is determined in this step S206 to be equal to or greater than the third threshold value ("NO" in step S206), the process is moved to step S211 to determine that the execution condition of the limiting process is not satisfied. When the value representing the possibility of achieving the goal of exercise is determined to be less than the third threshold value in step S206 ("YES" in step S206), then step S204 is performed. When the heart rate is determined to be less than the first threshold value in this step S204 ("NO" in step S204), then step S209 may be performed instead of step S211.

In this variation, step S204, which is related to determining the second condition, may be omitted.

Moreover, step S205, which is related to determining the third condition, may be omitted. When step S205 is omitted, step S209 is also omitted.

Furthermore, step S207, which is related to determining the fifth condition, may be omitted. When step S207 is omitted, step S210 is also omitted.

In addition, steps S209 and S210 may be omitted, with step S211 being performed instead of steps S209 and S210 (in other words, the satisfied first condition may not be a requirement for the satisfied execution condition).

Furthermore, any two or more of the above omission of step S204, omission of step S205, omission of step S207, and omission of steps S209 and S210 may be combined.

(Variation 5)

The execution condition of the limiting process may be configured to be satisfied on the condition that at least the fifth condition is satisfied. In this case, for example, when step S207 is performed before step S204 of the execution condition determination process illustrated in FIG. 9 and the full marathon completion time is determined in this step S207 to be less than three hours and 30 minutes ("NO" in step S207), the process is moved to step S211 to determine that the execution condition of the limiting process is not satisfied. When the full marathon completion time is determined to be equal to or longer than three hours and 30 minutes ("YES" in step S207), then step S204 is performed. When the heart rate is determined to be less than the first threshold value in this step S204 ("NO" in step S204), step S209 may be performed instead of step S211.

In this variation, step S204, which is related to determining the second condition, may be omitted.

Moreover, step S205, which is related to determining the third condition, may be omitted. When step S205 is omitted, step S209 is also omitted.

Furthermore, step S206, which is related to determining the fourth condition, may be omitted. When step S206 is omitted, step S210 is also omitted.

In addition, steps S209 and S210 may be omitted, with step S211 being performed instead of steps S209 and S210 (in other words, the satisfied first condition may not be a requirement for the satisfied execution condition).

Furthermore, any two or more of the above omission of step S204, omission of step S205, omission of step S206, and omission of steps S209 and S210 may be combined.

(Variation 6)

When at least any one or at least specific one of the second to fifth conditions is determined to be satisfied before the start of the exercise or before the first warning is given after the start of the exercise, the normal range R may be adjusted (in other words, there may be set the "adjusted upper limit of the normal range" and the "adjusted lower limit of the normal range" in the warning setting data 132). The adjustment in this case may be an adjustment for widening the normal range R.

For example, when the user U inputs "the fatigue level is high" or "the physical condition is poor" in the dialog screen for inputting the fatigue level or the physical condition of the user U described above before the start of exercise, the second condition is determined to be satisfied, and the normal range R at the start point of the exercise may be adjusted in advance.

When the content of the exercise having been started is not a certain content (for example, when the pace is slower than the second threshold value), the third condition is determined to be satisfied, and the normal range R may be adjusted in advance before the first warning is given.

When the value representing the possibility of achieving the goal related to the exercise of the user U is determined to be less than the predetermined third threshold value, before the start of the exercise or before the first warning is given after the start of the exercise, then the fourth condition is determined to be satisfied, and the normal range R may be adjusted in advance before the start of the exercise or before the first warning is given.

When the athletic ability of the user U is determined not to meet the given criterion on the basis of the full marathon completion time or the like, the normal range R may be adjusted in advance before the start of the exercise or before the first warning is given.

The adjustment of the normal range R in this variation is also included in the "limiting process."

(Variation 7)

In at least one of steps S111 and S116 of the warning process illustrated in FIG. 6, a process to make the warning by the warning function weaker than the warning by the normal warning function may be performed, instead of stopping the warning. For example, the warning display by the display unit 141 may be switched to a display that is more difficult for the user U to see. Moreover, the audio volume for warnings output by the audio output unit 142 may be reduced. The intensity of vibration for warnings by the vibration unit 143 may be reduced. The process of making the warning by the warning function weaker than the warning by the normal warning function is a mode for the limiting process of limiting the warning function.

As a first mode for variation 7, when the number of times the limiting process is performed after the start of the exercise is less than the reference number of times ("YES" in step S109 of FIG. 6), the process of making the warning weaker than the warning by the normal warning function may be performed in step S111. Specifically, the process of weakening the warning may be performed as the limiting process, instead of the process of adjusting the normal range R and the process of stopping the warning. In addition to the process of weakening the warning performed at the start point of step S111, the process of setting the next warning to be weakened may also be performed. In this first mode, "the reference number of times" is defined as "the maximum number of times to perform the process of weakening the warning." When it is determined in step S109 that the number of times the process of weakening the warning has been performed reaches the reference number of times ("NO" in step S109), the warning in progress is stopped in step S116.

As a second mode for variation 7, when the number of times the limiting process is performed after the start of the exercise is less than the reference number of times ("YES" in step S109 of FIG. 6), the normal range R may be adjusted in step S110 and then the process of making the warning weaker than the warning of the normal warning function may be performed in step S111. In this case, in step S111, a process of weakening the warning in progress may be performed, a process of setting the next warning to be weakened may be performed, or both these processes may be performed. In the second mode for variation 7, the entire process of steps S110 and S111, including the process of adjusting the normal range R and the process of weakening the warning, corresponds to one limiting process.

As a third mode for variation 7, in step S116, which is performed in the case where the number of times the limiting process has been performed (variable n) reaches the reference number of times ("NO" in step S109), the process of weakening the warning may be performed, instead of the process of stopping the warning. In this case, after the completion of step S116, the following processes are performed: a process of determining whether the warning target index falls within the normal range R; and a process of stopping the weakened warning when the warning target index is determined to fall within the normal range R. The third mode may be combined with the first or second mode described in the above.

<Effects>

As described above, an information processing method according to this embodiment is an information processing method performed by the CPU 11 (computer), the method including: determining whether an execution condition is satisfied (steps S107 and S108 in FIG. 6), the execution condition including at least one of a first condition (steps S202, S203, S209, and S210 in FIG. 7) related to the length of time during which a warning is generated by a predetermined normal warning function as a warning function related to the exercise state of the user U when performing a certain exercise; a second condition (step S204) related to the fatigue level of the user U; a third condition (step S205) that the content of the above certain exercise being performed by the user U is not a certain content; a fourth condition (step S206) related to the possibility of achieving the goal related to the certain exercise of the user U; and a fifth condition (step S207) related to an athletic ability of the user U; and performing a limiting process of controlling the warning function so that the warning is more limited than in the case of the normal warning function (steps S110, S111, and S116) on the condition that the execution condition is satisfied ("YES" in step S108).

By performing the limiting process on the condition that the execution condition including the first condition is satisfied, the warnings are able to be limited so as to prevent a continuation of warnings unnecessary for the user U after the user U recognizes the warning.

Moreover, by performing the limiting process on the condition that the execution condition including the second condition is satisfied, the warnings are able to be limited so as to prevent warnings that the user U finds inappropriate, in the case where the fatigue level of the user U is high and it is difficult for the user U to exercise in the exercise state where the warning can be cancelled.

Moreover, by performing the limiting process on the condition that the execution condition including the third condition is satisfied, the warnings are able to be limited so as to prevent warnings that the user U finds inappropriate, in the case where the exercise state can be assumed to be difficult to improve to a state where no warning is given for some reason, such as fatigue or ambient conditions.

Furthermore, by performing the limiting process on the condition that the execution condition including the fourth condition is satisfied, the warnings are able to be limited so as to prevent warnings that the user U finds inappropriate in the case where the user U is likely to be in a condition where the goal cannot be achieved and the exercise state can be assumed to be difficult to improve to the state where no warning is given.

Still further, by performing the limiting process on the condition that the execution condition including the fifth condition is satisfied, the warnings are able to be limited so as to prevent warnings that the user U fins inappropriate in the case where the exercise state can be assumed to be difficult to improve to the state where no warning is given, from the viewpoint of the athletic ability of the user U.

Therefore, the warning function is able to be limited more appropriately according to the exercise state of the user U and so on. Moreover, limiting unnecessary warnings enables a reduction in the annoyance felt by the user U. In addition, it enables a reduction in the power consumption of the terminal device 10.

Moreover, the first condition is conditional on that the duration of a warning generated by the normal warning function as a warning function or the total time during which warnings are generated by the normal warning function within a certain period of time has reached the determination time. This enables the warnings to be limited by determining that the warnings are unnecessary for the user U, in the case where the warnings continue continuously or in the case where the warnings continue intermittently.

An adjustment is made to increase the determination time (steps S209 and S210) in at least any one of: a case where the heart rate of the user U when performing the above certain exercise is less than the predetermined first threshold value ("NO" in step S204 of FIG. 7); a case where the value corresponding to the moving speed of the user U in the above certain exercise involving the movement of the user U is a predetermined second threshold value or a value faster than the second threshold value ("NO" in step S205); a case where the value representing the possibility of achieving the goal related to the above certain exercise of the user U is equal to or greater than a predetermined third threshold value ("NO" in step S206); and a case where the athletic ability of the user U represented by the athletic ability information representing the athletic ability of the user U meets the given criterion ("NO" in step S207). This enables the duration of warnings from being limited more than necessary in the case where the fatigue level of the user U is assumed to be not so high or in the case where the user U is assumed to be running comfortably.

The athletic ability information representing the athletic ability of the user U is acquired (step S207 in FIG. 7), and the higher the athletic ability of the user U represented by the acquired athletic ability information is, the longer the determination time is set (step S210). When the athletic ability of the user U is high, it can be assumed that the user U is exercising comfortably and that it is easy to improve the exercise state to a state where no warning is given. Therefore, the higher the athletic ability of the user U is, the longer the determination time is set, and the longer the time period during which the warnings are given, the more effectively the exercise state is able to be improved. On the other hand, in the case where the athletic ability of the user U is low, it can be assumed that the user U is exercising uncomfortably and that it is difficult to improve the exercise state to the state where no warning is given. Therefore, the lower the athletic ability of the user U is, the shorter the determination time is set so that the warning time is shorter, thereby enabling the warning that the user U finds inappropriate to be limited earlier and enabling a reduction in the annoyance felt by the user U.

In addition, the second condition is determined based on the biometric information of the user U when performing the certain exercise (step S204 in FIG. 7). This enables the fatigue level of the user U to be estimated more appropriately.

Moreover, the second condition is conditional on that the heart rate of the user U as the biometric information is equal to or greater than the predetermined first threshold value (step S204 of FIG. 7). The heart rate is able to be easily acquired by the terminal device worn by the user U for use, thereby enabling determination of whether the second condition is satisfied without using a large-scale device.

The certain exercise is accompanied by the movement of the user U and, in the case where the pace (a value corresponding to the moving speed) of the user U in the certain exercise is slower than a predetermined second threshold value, the content of the certain exercise is determined to be not a certain content (step S205 in FIG. 7). The use of the pace as described above enables easy estimation of a fact that, for some reason, it is difficult for the user U to improve the exercise state to a state where no warning is given.

A fact that a value representing the possibility of achieving the goal related to the certain exercise of the user U is less than a predetermined third threshold value is determined as the fourth condition included in the execution condition (step S206 in FIG. 7). When the value representing the possibility of achieving the goal is less than the third threshold value, it is assumed that the user U is likely to be in a condition where he/she is not able to achieve the goal and that, for some reason, it is difficult to improve the exercise state to a condition where no warning is given. In this case, the warnings are limited by determining that the fourth condition is satisfied, thereby enabling suppression of warnings that the user U finds inappropriate and enabling a reduction in the annoyance felt by the user U.

The fifth condition is conditional on that the athletic ability of the user U does not meet the given criterion (step S207 in FIG. 7). Unless the athletic ability of the user U meets the given criterion, it can be assumed that it is difficult to improve the exercise state to a state where no warning is given from the viewpoint of the athletic ability of the user U. In such a case, the fifth condition is determined to be satisfied and the warnings are limited, thereby enabling the limitation of the warnings that the user U finds inappropriate and enabling a reduction in the annoyance felt by the user U.

The warning by the warning function is stopped (steps S111 and S116 in FIG. 6) or the warning by the warning function is made weaker than the warning by the normal warning function by performing the limiting process. Stopping the warning securely reduces the annoyance of the warning felt by the user U. Moreover, weakening the warning enables the annoyance felt by the user U to be alleviated while making the user U aware of the warning in progress.

The warning function generates a warning when the exercise state of the user U is out of the normal range R related to the normal warning function (steps S105 and S106 in FIG. 6). Then, the limiting process is performed to adjust the normal range R so that the warning is less likely to be generated than in the case of the normal warning function (step S110). This enables appropriate warnings according to the situation of the exercise of the user U.

Furthermore, the warning function generates a warning when the exercise state of the user U is out of the normal range R related to the normal warning function (steps S105 and S106 in FIG. 6). In the case where the number of times the limiting process is performed after the start of the certain exercise is less than the reference number of times ("YES" in step S109), the normal range R is adjusted (step S110) in the next limiting process so that the warning is less likely to be generated than the normal range R immediately before the next limiting process is performed. In the case where the reference number of limiting processes have already been performed since the start of the certain exercise ("NO" in step S109), the warning by the warning function is stopped in the next limiting process (step S116) or the warning by the warning function is made weaker than in the case of the normal warning function. Thereby, in the case where a warning is still generated even after adjusting the normal range R as described above while adjusting the normal range R to some extent so that an appropriate warning is performed according to the change in the situation of the exercise of the user U, the warning is stopped or the warning is made weaker, thereby enabling a reduction in the annoyance felt by the user U.

An exercise application 131 (program) according to this embodiment causes the CPU 11 (computer) to perform: a process of determining whether an execution condition is satisfied (steps S107 and S108 in FIG. 6), the execution condition including at least one of a first condition (steps S202, S203, S209, and S210 in FIG. 7) related to the length of time during which a warning is generated by a predetermined normal warning function as a warning function related to the exercise state of the user U when performing a certain exercise; a second condition (step S204) related to the fatigue level of the user U; a third condition (step S205) that the content of the above certain exercise being performed by the user U is not a certain content; a fourth condition (step S206) related to the possibility of achieving the goal related to the certain exercise of the user U; and a fifth condition (step S207) related to an athletic ability of the user U; and a process of performing a limiting process of controlling the warning function so that the warning is more limited than in the case of the normal warning function (steps S110, S111, and S116) on the condition that the execution condition is satisfied ("YES" in step S108). This enables the warning function to be limited more appropriately according to the exercise situation or the like of the user U. Moreover, limiting unnecessary warnings enables a reduction in the annoyance felt by the user U. In addition, it enables a reduction in the power consumption of the terminal device 10.

In addition, the terminal device 10 (information processing device) according to this embodiment includes a CPU 11 (computer) that performs: a process of determining whether an execution condition is satisfied (steps S107 and S108 in FIG. 6), the execution condition including at least one of a first condition (steps S202, S203, S209, and S210 in FIG. 7) related to the length of time during which a warning is generated by a predetermined normal warning function as a warning function related to the exercise state of the user U when performing a certain exercise; a second condition (step S204) related to the fatigue level of the user U; a third condition (step S205) that the content of the above certain exercise being performed by the user U is not a certain content; a fourth condition (step S206) related to the possibility of achieving the goal related to the certain exercise of the user U; and a fifth condition (step S207) related to an athletic ability of the user U; and a limiting process of controlling the warning function so that the warning is more limited than in the case of the normal warning function (steps S110, S111, and S116) on the condition that the execution condition is satisfied ("YES" in step S108). This enables the warning function to be limited more appropriately according to the exercise situation or the like of the user U. Moreover, limiting unnecessary warnings enables a reduction in the annoyance felt by the user U. In addition, it enables a reduction in the power consumption of the terminal device 10.

<Others>

The description in the above embodiment is merely an example of the information processing method, program, and information processing device according to the present disclosure, and the invention is not limited thereto.

For example, when the functions implemented by the sensor device 20 in the above embodiment are able to be implemented by the terminal device 10, the sensor device 20 may be omitted.

The location where the sensor device 20 is worn is not limited to the waist. For example, the sensor device may be a wrist-type terminal worn on the user's wrist. In this case, the kinematic index is able to be used to detect the swing of the user's arms or the like.

In the above embodiment, the normal range R is adjusted at least once in the limiting process, as an example, in the description. The present disclosure, however, is not limited thereto. In the first limiting process performed after the start of the exercise, the warning by the warning function may be stopped, or the warning by the warning function may be made weaker than in the case of the normal warning function. Specifically, the "reference number of times for normal range adjustment" in the warning setting data 132 may be set to "0."

Although the heart rate is given as an example of biometric information of the subject, the biometric information is not limited to the heart rate, as long as it has a correlation with the fatigue level of the user U. For example, blood oxygen saturation (blood oxygen concentration) or the maximum oxygen uptake (the maximum amount of oxygen that can be taken into the body per minute) may be used as the biometric information.

In situations where the goal is to achieve or reduce running time, such as in the case of running a short distance as exercise or running a marathon or performing other competitive event as exercise, the limiting process of limiting warnings may not be performed. This enables the warning to be given as set as desired by the user U in the situations where the goal is to achieve or reduce the running time. Alternatively, in the situations where the goal is to achieve or reduce the running time, the reference number of times the normal range R is adjusted as a limiting process may be reduced from normal.

Moreover, when it is determined, with reference to the exercise state when the user U was injured in the past and based on the adjustment status of the normal range R of the warning target index, that the running of the user U is similar to the exercise state of the user U being injured, there may be given a warning indicating that the user U is in an exercise state that is likely to cause injury, instead of (or in addition to) the warning by the normal warning function.

Although walking and running are exemplified as the exercise performed by the user U, the exercise is not limited thereto. For example, it may be bicycle riding, swimming, or the like. In addition, the exercise is not necessarily limited to an exercise involving movement, but may be gymnastics or strength training.

The subject that performs an exercise is not limited to a person, as long as it is capable of performing an exercise. For example, the subject may be an animal or a robot. In the case where the subject is a robot, the warning function includes a function to send a signal related to the warning to a robot or to a control unit that controls the robot's operation. Moreover, in the case where the subject is a robot, the fatigue level of the robot may be expressed by the cumulative value of a load applied to a certain part of the robot according to the exercise.

In the above description, there has been disclosed an example in which the memories 13 and 23 are used as computer-readable media for the program according to the present disclosure, but it is not limited thereto. As other computer-readable media, information storage media such as an HDD, an SSD, a flash memory, and a CD-ROM may be applied. Carrier waves are also applicable to the present disclosure as a medium for providing data of the program according to the present disclosure via a communication line.

It is naturally possible to appropriately modify the detailed configuration and detailed operation of the components of the terminal device 10 and the sensor device in the above embodiments to the extent not to depart from the gist of the present disclosure.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-152858, filed Sep. 21, 2021 which is hereby incorporated by reference wherein in its entirety.

What is claimed is:
1. An information processing device, comprising:
one or more processors; and
one or more memories storing a program to be executed by the one or more processors;
wherein the program causes the one or more processors to perform the following:
determining whether an execution condition is satisfied, the execution condition including a first condition related to a length of time during which a warning is generated by a predetermined normal warning function as a warning function related to an exercise state of a subject when performing a certain exercise; and
performing, on the condition that the execution condition is satisfied, a limiting process of controlling the warning function so that the warning is more limited than in the case of the normal warning function;
wherein:
the warning function generates the warning when the exercise state of the subject is out of a normal range related to the normal warning function; and
in the case where a number of times the limiting process is performed after a start of the certain exercise is less than a reference number of times, the normal range is adjusted in the next limiting process so that the warning is less likely to be generated than the normal range immediately before the next limiting process is performed.

2. The information processing device according to claim 1, wherein the first condition is conditional on that a duration of the warning generated by the normal warning function as a warning function or a total time during which warnings are generated by the normal warning function within a certain period of time has reached a determination time.

3. The information processing device according to claim 2, wherein an adjustment is made to increase the determination time in at least any one of:

a case where a heart rate of the subject when performing the certain exercise is less than a predetermined first threshold value;

a case where a value corresponding to a moving speed of the subject in the certain exercise involving a movement of the subject is a predetermined second threshold value or a value faster than the second threshold value;

a case where a value representing a possibility of achieving a goal related to the certain exercise of the subject is equal to or greater than a predetermined third threshold value; and a case where an athletic ability of the subject represented by athletic ability information representing the athletic ability of the subject meets a given criterion.

4. The information processing device according to claim 2, wherein:

athletic ability information representing the athletic ability of the subject is acquired; and the higher the athletic ability of the subject represented by the acquired athletic ability information is, the longer the determination time is set.

5. The information processing device according to claim 1, wherein the execution condition further includes a second condition related to the fatigue level of the subject, and wherein the second condition is determined based on biometric information of the subject when performing the certain exercise.

6. The information processing device according to claim 5, wherein the second condition is conditional on that a heart rate of the subject as the biometric information is equal to or greater than the predetermined first threshold value.

7. The information processing device according to claim 1, wherein:

a certain exercise is accompanied by a movement of the subject;

the execution condition further includes a third condition that a content of the certain exercise being performed by the subject is not a certain content; and in the case where a value corresponding to a moving speed of the subject in the certain exercise is slower than a predetermined second threshold value, the content of the certain exercise is determined to be not a certain content.

8. The information processing device according to claim 1, wherein the execution condition further includes a fourth condition related to a possibility of achieving a goal related to the certain exercise of the subject, and wherein a fact that a value representing the possibility of achieving the goal related to the certain exercise of the subject is less than the predetermined third threshold value is determined as the fourth condition.

9. The information processing device according to claim 1, wherein the execution condition further includes a fifth condition related to an athletic ability of the subject, and the fifth condition is conditional on that the athletic ability of the subject does not meet a given criterion.

10. The information processing device according to claim 1, wherein the warning by the warning function is stopped or the warning by the warning function is made weaker than the warning by the normal warning function by performing the limiting process.

11. The information processing device according to claim 1, wherein:

the limiting process is performed to adjust the normal range so that the warning is less likely to be generated than in the case of the normal warning function.

12. The information processing device according to claim 1, wherein:

in the case where the reference number of limiting processes have already been performed since the start of the certain exercise, the warning by the warning function is stopped in the next limiting process or the warning by the warning function is made weaker than in the case of the normal warning function.

13. The information processing device according to claim 1, wherein it is determined whether the execution condition including the first condition, and further including at least one of a second condition related to the fatigue level of the subject, a third condition that a content of the certain exercise being performed by the subject is not a certain content, a fourth condition related to a possibility of achieving a goal related to the certain exercise of the subject, or a fifth condition related to an athletic ability of the subject, is satisfied in determining whether the execution condition is satisfied.

14. A method performed by one or more processors of an information processing device, the method comprising:

determining whether an execution condition is satisfied, the execution condition including a first condition related to a length of time during which a warning is generated by a predetermined normal warning function as a warning function related to an exercise state of a subject when performing a certain exercise; and performing, on the condition that the execution condition is satisfied, a limiting process of controlling the warning function so that the warning is more limited than in the case of the normal warning function;

wherein:

the warning function generates the warning when the exercise state of the subject is out of a normal range related to the normal warning function; and in the case where a number of times the limiting process is performed after a start of the certain exercise is less than a reference number of times, the normal range is adjusted in the next limiting process so that the warning is less likely to be generated than the normal range immediately before the next limiting process is performed.

15. The information processing method according to claim 14, wherein the first condition is conditional on that a duration of a warning generated by the normal warning function as a warning function or a total time during which warnings are generated by the normal warning function within a certain period of time has reached a determination time.

16. The information processing method according to claim 15, further comprising making an adjustment to increase the determination time in at least any one of:

a case where a heart rate of a subject when performing the certain exercise is less than a predetermined first threshold value;

a case where a value corresponding to a moving speed of the subject in the certain exercise involving a movement of the subject is a predetermined second threshold value or a value faster than the second threshold value;

a case where a value representing a possibility of achieving a goal related to the certain exercise of the subject is equal to or greater than a predetermined third threshold value; and a case where an athletic ability of the subject represented by athletic ability information representing the athletic ability of the subject meets a given criterion.

17. The information processing method according to claim 15, further comprising:

acquiring athletic ability information representing the athletic ability of the subject; and setting the determination time longer as the athletic ability of the subject represented by the acquired athletic ability information is higher.

18. A non-transitory computer readable storage medium, storing a program executable by one or more processors in an information processing device, the program causing the one or more processors to perform:

determining whether an execution condition is satisfied, the execution condition including a first condition related to a length of time during which a warning is generated by a predetermined normal warning function as a warning function related to an exercise state of a subject when performing a certain exercise; and performing, on the condition that the execution condition is satisfied, a limiting process of controlling the warning function so that the warning is more limited than in the case of the normal warning function;

wherein:

the warning function generates the warning when the exercise state of the subject is out of a normal range related to the normal warning function; and in the case where a number of times the limiting process is performed after a start of the certain exercise is less than a reference number of times, the normal range is adjusted in the next limiting process so that the warning is less likely to be generated than the normal range immediately before the next limiting process is performed.

19. The non-transitory computer readable storage medium according to claim 18, wherein the first condition is conditional on that a duration of a warning generated by the normal warning function as a warning function or the total time during which warnings are generated by the normal warning function within a certain period of time has reached a determination time.

20. The non-transitory computer readable storage medium according to claim 19, the program causing the one or more processors further to perform adjustment to increase the determination time in at least any one of:

a case where a heart rate of the subject when performing the certain exercise is less than a predetermined first threshold value;

a case where a value corresponding to a moving speed of the subject in the certain exercise involving a movement of the subject is a predetermined second threshold value or a value faster than the second threshold value;

a case where a value representing a possibility of achieving a goal related to the certain exercise of the subject is equal to or greater than a predetermined third threshold value; and a case where an athletic ability of the subject represented by athletic ability information representing the athletic ability of the subject meets a given criterion.

21. The non-transitory computer readable storage medium according to claim 19, the program causing the one or more processors further to perform:

acquiring athletic ability information representing the athletic ability of the subject; and setting the determination time longer as the athletic ability of the subject represented by the acquired athletic ability information is higher.

* * * * *